(12) United States Patent
Richter et al.

(10) Patent No.: US 7,888,098 B2
(45) Date of Patent: Feb. 15, 2011

(54) SCALABLE PROCESS FOR PROTEIN PURIFICATION

(75) Inventors: Susanne Richter, Schlieren (CH); Simon Topell, Zurich (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 132 days.

(21) Appl. No.: 11/922,591

(22) PCT Filed: Jun. 20, 2006

(86) PCT No.: PCT/EP2006/063373

§ 371 (c)(1),
(2), (4) Date: Dec. 20, 2007

(87) PCT Pub. No.: WO2006/136566

PCT Pub. Date: Dec. 28, 2006

(65) Prior Publication Data

US 2009/0048433 A1    Feb. 19, 2009

(30) Foreign Application Priority Data

Jun. 21, 2005    (EP) ................................ 05105513

(51) Int. Cl.
*C12N 7/02*    (2006.01)
*C07K 1/18*    (2006.01)

(52) U.S. Cl. ...................... 435/239; 530/416

(58) Field of Classification Search ........................ None
See application file for complete search history.

(56) References Cited

U.S. PATENT DOCUMENTS

| 5,141,857 | A | * | 8/1992 | DiFrancesco | ................ 435/194 |
| 5,820,870 | A | * | 10/1998 | Joyce et al. | .............. 424/204.1 |
| 6,261,823 | B1 | | 7/2001 | Tang et al. | |
| 2004/0076611 | A1 | * | 4/2004 | Bachmann et al. | ......... 424/93.2 |

FOREIGN PATENT DOCUMENTS

| WO | WO 96/27677 A2 | 9/1996 |
| WO | WO 00/09671 | * 2/2000 |
| WO | WO 01/28583 A2 | 4/2001 |
| WO | WO 01/28585 A1 | 4/2001 |
| WO | WO 01/92552 A2 | 12/2001 |
| WO | WO 02/44348 A2 | 6/2002 |
| WO | WO 2004/020971 A2 | 3/2004 |

OTHER PUBLICATIONS

Nardelli et al, Infection And Immunity, 65: 3328-3336, 1997).*
Brown, W.L., et al., "RNA Bacteriophage Capsid-mediated Drug Delivery and Epitope Presentation," *Intervirology* 45:371-380, S. Karger AG, Basel, Switzerland (2002).
Legendre, D., and Fastrez, J., "Production in *Saccharomyces cerevisiae* of MS2 virus-like particles packaging functional heterologous mRNAs," *J. Biotechnol.* 117:183-194, Elsevier B.V., Amsterdam, Netherlands (2005).
Tsuru, S., et al., "Adsorption and Preparation of Human Viruses Using Hydroxyapatite Column," *Bio-Med. Mater. Eng.* 1:143-147, Pergamon Press, United States (1991).
Vasiljeva, I., et al., "Mosaic Qβ coats as a new presentation model," *FEBS Lett.* 431:7-11, Federation of European Biochemical Societies, Amsterdam, Netherlands (1998).
Zhang, W., et al., "Expression of Human Papillomavirus Type 16 L1 Protein in *Escherichia coli*: Denaturation, Renaturation, and Self-assembly of Virus-like Particles *in Vitro*," *Virol.* 243:423-431, Academic Press, United States (1998).
International Search Report for International Application No. PCT/EP2006/063373, European Patent Office, mailed on Aug. 11, 2006.
The Written Opinion of the International Searching Authority for International Application No. PCT/EP2006/063373, European Patent Office, mailed on Dec. 21, 2007.

* cited by examiner

*Primary Examiner*—Mary E Mosher
(74) *Attorney, Agent, or Firm*—Sterne, Kessler, Goldstein & Fox P.L.L.C.

(57) ABSTRACT

The invention provides a process for the purification recombinantly expressed, self-assembled VLP from the homogenate of a bacterial host, wherein the process can be scaled up to a commercial production scale in a cost effective manner. The process comprises a first chromatography using an anion exchange matrix, a second chromatography using hydroxyapatite and, optionally, a size exclusion chromatography. VLP preparations obtained by the process of the invention are essentially free of endotoxin contaminations.

20 Claims, No Drawings

SEQUENCE LISTING

<160> NUMBER OF SEQ ID NOS: 23

<210> SEQ ID NO 1
<211> LENGTH: 185
<212> TYPE: PRT
<213> ORGANISM: Hepatitis B virus

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185

<210> SEQ ID NO 2
<211> LENGTH: 188
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys

```
                35                  40                  45
Ser Pro His His Thr Ala Leu Arg Gln Ala Ile Leu Cys Trp Gly Asp
 50                  55                  60

Leu Met Thr Leu Ala Thr Trp Val Gly Thr Asn Leu Glu Asp Gly Gly
 65                  70                  75                  80

Lys Gly Gly Ser Arg Asp Leu Val Val Ser Tyr Val Thr Asn Val
                 85                  90                  95

Gly Leu Lys Phe Arg Gln Leu Leu Trp Phe His Ile Ser Cys Leu Thr
                100                 105                 110

Phe Gly Arg Glu Thr Val Leu Glu Tyr Leu Val Ser Phe Gly Val Trp
                115                 120                 125

Ile Arg Thr Pro Pro Ala Tyr Arg Pro Asn Ala Pro Ile Leu Ser
130                 135                 140

Thr Leu Pro Glu Thr Thr Val Val Arg Arg Asp Arg Gly Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Arg Glu Ser Gln Cys
            180                 185

<210> SEQ ID NO 3
<211> LENGTH: 132
<212> TYPE: PRT
<213> ORGANISM: Bacteriophage Qbeta

<400> SEQUENCE: 3

Ala Lys Leu Glu Thr Val Thr Leu Gly Asn Ile Gly Lys Asp Gly Lys
 1               5                  10                  15

Gln Thr Leu Val Leu Asn Pro Arg Gly Val Asn Pro Thr Asn Gly Val
                20                  25                  30

Ala Ser Leu Ser Gln Ala Gly Ala Val Pro Ala Leu Glu Lys Arg Val
                35                  40                  45

Thr Val Ser Val Ser Gln Pro Ser Arg Asn Arg Lys Asn Tyr Lys Val
 50                  55                  60

Gln Val Lys Ile Gln Asn Pro Thr Ala Cys Thr Ala Asn Gly Ser Cys
 65                  70                  75                  80

Asp Pro Ser Val Thr Arg Gln Ala Tyr Ala Asp Val Thr Phe Ser Phe
                 85                  90                  95

Thr Gln Tyr Ser Thr Asp Glu Glu Arg Ala Phe Val Arg Thr Glu Leu
                100                 105                 110

Ala Ala Leu Leu Ala Ser Pro Leu Leu Ile Asp Ala Ile Asp Gln Leu
            115                 120                 125

Asn Pro Ala Tyr
        130

<210> SEQ ID NO 4
<211> LENGTH: 329
<212> TYPE: PRT
<213> ORGANISM: Bacteriophage Qbeta

<400> SEQUENCE: 4

Met Ala Lys Leu Glu Thr Val Thr Leu Gly Asn Ile Gly Lys Asp Gly
 1               5                  10                  15

Lys Gln Thr Leu Val Leu Asn Pro Arg Gly Val Asn Pro Thr Asn Gly
                20                  25                  30

Val Ala Ser Leu Ser Gln Ala Gly Ala Val Pro Ala Leu Glu Lys Arg
```

```
                35                  40                  45
Val Thr Val Ser Val Ser Gln Pro Ser Arg Asn Arg Lys Asn Tyr Lys
 50                  55                  60

Val Gln Val Lys Ile Gln Asn Pro Thr Ala Cys Thr Ala Asn Gly Ser
 65                  70                  75                  80

Cys Asp Pro Ser Val Thr Arg Gln Ala Tyr Ala Asp Val Thr Phe Ser
                 85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr Trp Thr Leu Leu Ile Ala Gly Gly Gly Ser Gly
130                 135                 140

Ser Lys Pro Asp Pro Val Ile Pro Asp Pro Pro Ile Asp Pro Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
        195                 200                 205

Gly Asn Thr Lys Trp Arg Asp Trp Asp Ser Arg Leu Ser Tyr Thr Thr
210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325

<210> SEQ ID NO 5
<211> LENGTH: 129
<212> TYPE: PRT
<213> ORGANISM: Bacteriophage R17

<400> SEQUENCE: 5

Ala Ser Asn Phe Thr Gln Phe Val Leu Val Asn Asp Gly Gly Thr Gly
 1               5                  10                  15

Asn Val Thr Val Ala Pro Ser Asn Phe Ala Asn Gly Val Ala Glu Trp
                20                  25                  30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
        50                  55                  60

Pro Lys Val Ala Thr Gln Thr Val Gly Gly Val Glu Leu Pro Val Ala
65                  70                  75                  80
```

```
Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 6
<211> LENGTH: 130
<212> TYPE: PRT
<213> ORGANISM: Bacteriophage fr

<400> SEQUENCE: 6

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Asn Asn Arg Lys Tyr Thr Val Lys Val Glu
    50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe
                85                  90                  95

Ala Thr Asn Asp Asp Cys Ala Leu Ile Val Lys Ala Leu Gln Gly Thr
            100                 105                 110

Phe Lys Thr Gly Asn Pro Ile Ala Thr Ala Ile Ala Ala Asn Ser Gly
        115                 120                 125

Ile Tyr
    130

<210> SEQ ID NO 7
<211> LENGTH: 130
<212> TYPE: PRT
<213> ORGANISM: Bacteriophage GA

<400> SEQUENCE: 7

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Lys Tyr Ala Ile Lys Leu Glu Val
    50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
```

130

<210> SEQ ID NO 8
<211> LENGTH: 132
<212> TYPE: PRT
<213> ORGANISM: Bacteriophage SP

<400> SEQUENCE: 8

Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Phe Lys
    50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
        130

<210> SEQ ID NO 9
<211> LENGTH: 329
<212> TYPE: PRT
<213> ORGANISM: Bacteriophage SP

<400> SEQUENCE: 9

Ala Lys Leu Asn Gln Val Thr Leu Ser Lys Ile Gly Lys Asn Gly Asp
1               5                   10                  15

Gln Thr Leu Thr Leu Thr Pro Arg Gly Val Asn Pro Thr Asn Gly Val
            20                  25                  30

Ala Ser Leu Ser Glu Ala Gly Ala Val Pro Ala Leu Glu Lys Arg Val
        35                  40                  45

Thr Val Ser Val Ala Gln Pro Ser Arg Asn Arg Lys Asn Phe Lys Val
    50                  55                  60

Gln Ile Lys Leu Gln Asn Pro Thr Ala Cys Thr Arg Asp Ala Cys Asp
65                  70                  75                  80

Pro Ser Val Thr Arg Ser Ala Phe Ala Asp Val Thr Leu Ser Phe Thr
                85                  90                  95

Ser Tyr Ser Thr Asp Glu Glu Arg Ala Leu Ile Arg Thr Glu Leu Ala
            100                 105                 110

Ala Leu Leu Ala Asp Pro Leu Ile Val Asp Ala Ile Asp Asn Leu Asn
        115                 120                 125

Pro Ala Tyr Trp Ala Ala Leu Val Ala Ser Ser Gly Gly Gly Gly Asp
    130                 135                 140

Asn Pro Ser Asp Pro Asp Val Pro Val Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg

-continued

```
                180             185             190
Gly Asp Glu Val Ser Val Thr Phe Asp Tyr Ala Leu Glu Asp Phe Leu
        195                 200                 205
Gly Asn Thr Asn Trp Arg Asn Trp Asp Gln Arg Leu Ser Asp Tyr Asp
    210                 215                 220
Ile Ala Asn Arg Arg Arg Cys Arg Gly Asn Gly Tyr Ile Asp Leu Asp
225                 230                 235                 240
Ala Thr Ala Met Gln Ser Asp Asp Phe Val Leu Ser Gly Arg Tyr Gly
                245                 250                 255
Val Arg Lys Val Lys Phe Pro Gly Ala Phe Gly Ser Ile Lys Tyr Leu
            260                 265                 270
Leu Asn Ile Gln Gly Asp Ala Trp Leu Asp Leu Ser Glu Val Thr Ala
        275                 280                 285
Tyr Arg Ser Tyr Gly Met Val Ile Gly Phe Trp Thr Asp Ser Lys Ser
    290                 295                 300
Pro Gln Leu Pro Thr Asp Phe Thr Gln Phe Asn Ser Ala Asn Cys Pro
305                 310                 315                 320
Val Gln Thr Val Ile Ile Pro Ser
                325

<210> SEQ ID NO 10
<211> LENGTH: 130
<212> TYPE: PRT
<213> ORGANISM: Bacteriophage MS2

<400> SEQUENCE: 10

Met Ala Ser Asn Phe Thr Gln Phe Val Leu Val Asp Asn Gly Gly Thr
1               5                   10                  15
Gly Asp Val Thr Val Ala Pro Ser Asn Phe Ala Asn Gly Val Ala Glu
            20                  25                  30
Trp Ile Ser Ser Asn Ser Arg Ser Gln Ala Tyr Lys Val Thr Cys Ser
        35                  40                  45
Val Arg Gln Ser Ser Ala Gln Asn Arg Lys Tyr Thr Ile Lys Val Glu
    50                  55                  60
Val Pro Lys Val Ala Thr Gln Thr Val Gly Gly Val Glu Leu Pro Val
65                  70                  75                  80
Ala Ala Trp Arg Ser Tyr Leu Asn Met Glu Leu Thr Ile Pro Ile Phe
                85                  90                  95
Ala Thr Asn Ser Asp Cys Glu Leu Ile Val Lys Ala Met Gln Gly Leu
            100                 105                 110
Leu Lys Asp Gly Asn Pro Ile Pro Ser Ala Ile Ala Ala Asn Ser Gly
        115                 120                 125
Ile Tyr
    130

<210> SEQ ID NO 11
<211> LENGTH: 133
<212> TYPE: PRT
<213> ORGANISM: Bacteriophage M11

<400> SEQUENCE: 11

Met Ala Lys Leu Gln Ala Ile Thr Leu Ser Gly Ile Gly Lys Lys Gly
1               5                   10                  15
Asp Val Thr Leu Asp Leu Asn Pro Arg Gly Val Asn Pro Thr Asn Gly
            20                  25                  30
Val Ala Ala Leu Ser Glu Ala Gly Ala Val Pro Ala Leu Glu Lys Arg
```

```
                35                  40                  45
Val Thr Ile Ser Val Ser Gln Pro Ser Arg Asn Arg Lys Asn Tyr Lys
             50                  55                  60

Val Gln Val Lys Ile Gln Asn Pro Thr Ser Cys Thr Ala Ser Gly Thr
 65                  70                  75                  80

Cys Asp Pro Ser Val Thr Arg Ser Ala Tyr Ser Asp Val Thr Phe Ser
                 85                  90                  95

Phe Thr Gln Tyr Ser Thr Val Glu Glu Arg Ala Leu Val Arg Thr Glu
                100                 105                 110

Leu Gln Ala Leu Leu Ala Asp Pro Met Leu Val Asn Ala Ile Asp Asn
            115                 120                 125

Leu Asn Pro Ala Tyr
        130

<210> SEQ ID NO 12
<211> LENGTH: 133
<212> TYPE: PRT
<213> ORGANISM: Bacteriophage MX1

<400> SEQUENCE: 12

Met Ala Lys Leu Gln Ala Ile Thr Leu Ser Gly Ile Gly Lys Asn Gly
 1               5                  10                  15

Asp Val Thr Leu Asn Leu Asn Pro Arg Gly Val Asn Pro Thr Asn Gly
             20                  25                  30

Val Ala Ala Leu Ser Glu Ala Gly Ala Val Pro Ala Leu Glu Lys Arg
         35                  40                  45

Val Thr Ile Ser Val Ser Gln Pro Ser Arg Asn Arg Lys Asn Tyr Lys
 50                  55                  60

Val Gln Val Lys Ile Gln Asn Pro Thr Ser Cys Thr Ala Ser Gly Thr
 65                  70                  75                  80

Cys Asp Pro Ser Val Thr Arg Ser Ala Tyr Ala Asp Val Thr Phe Ser
                 85                  90                  95

Phe Thr Gln Tyr Ser Thr Asp Glu Glu Arg Ala Leu Val Arg Thr Glu
                100                 105                 110

Leu Lys Ala Leu Leu Ala Asp Pro Met Leu Ile Asp Ala Ile Asp Asn
            115                 120                 125

Leu Asn Pro Ala Tyr
        130

<210> SEQ ID NO 13
<211> LENGTH: 330
<212> TYPE: PRT
<213> ORGANISM: Bacteriophage NL95

<400> SEQUENCE: 13

Met Ala Lys Leu Asn Lys Val Thr Leu Thr Gly Ile Gly Lys Ala Gly
 1               5                  10                  15

Asn Gln Thr Leu Thr Leu Thr Pro Arg Gly Val Asn Pro Thr Asn Gly
             20                  25                  30

Val Ala Ser Leu Ser Glu Ala Gly Ala Val Pro Ala Leu Glu Lys Arg
         35                  40                  45

Val Thr Val Ser Val Ala Gln Pro Ser Arg Asn Arg Lys Asn Tyr Lys
 50                  55                  60

Val Gln Ile Lys Leu Gln Asn Pro Thr Ala Cys Thr Lys Asp Ala Cys
 65                  70                  75                  80

Asp Pro Ser Val Thr Arg Ser Gly Ser Arg Asp Val Thr Leu Ser Phe
```

```
                    85                  90                  95
Thr Ser Tyr Ser Thr Glu Arg Glu Arg Ala Leu Ile Arg Thr Glu Leu
            100                 105                 110
Ala Ala Leu Leu Lys Asp Asp Leu Ile Val Asp Ala Ile Asp Asn Leu
            115                 120                 125
Asn Pro Ala Tyr Trp Ala Ala Leu Leu Ala Ala Ser Pro Gly Gly Gly
            130                 135                 140
Asn Asn Pro Tyr Pro Gly Val Pro Asp Ser Pro Asn Val Lys Pro Pro
145                 150                 155                 160
Gly Gly Thr Gly Thr Tyr Arg Cys Pro Phe Ala Cys Tyr Arg Arg Gly
                165                 170                 175
Glu Leu Ile Thr Glu Ala Lys Asp Gly Ala Cys Ala Leu Tyr Ala Cys
            180                 185                 190
Gly Ser Glu Ala Leu Val Glu Phe Glu Tyr Ala Leu Glu Asp Phe Leu
            195                 200                 205
Gly Asn Glu Phe Trp Arg Asn Trp Asp Gly Arg Leu Ser Lys Tyr Asp
            210                 215                 220
Ile Glu Thr His Arg Arg Cys Arg Gly Asn Gly Tyr Val Asp Leu Asp
225                 230                 235                 240
Ala Ser Val Met Gln Ser Asp Glu Tyr Val Leu Ser Gly Ala Tyr Asp
                245                 250                 255
Val Val Lys Met Gln Pro Pro Gly Thr Phe Asp Ser Pro Arg Tyr Tyr
                260                 265                 270
Leu His Leu Met Asp Gly Ile Tyr Val Asp Leu Ala Glu Val Thr Ala
            275                 280                 285
Tyr Arg Ser Tyr Gly Met Val Ile Gly Phe Trp Thr Asp Ser Lys Ser
            290                 295                 300
Pro Gln Leu Pro Thr Asp Phe Thr Arg Phe Asn Arg His Asn Cys Pro
305                 310                 315                 320
Val Gln Thr Val Ile Val Ile Pro Ser Leu
                325                 330

<210> SEQ ID NO 14
<211> LENGTH: 129
<212> TYPE: PRT
<213> ORGANISM: Bacteriophage f2

<400> SEQUENCE: 14

Ala Ser Asn Phe Thr Gln Phe Val Leu Val Asn Asp Gly Gly Thr Gly
1               5                   10                  15
Asn Val Thr Val Ala Pro Ser Asn Phe Ala Asn Gly Val Ala Glu Trp
            20                  25                  30
Ile Ser Ser Asn Ser Arg Ser Gln Ala Tyr Lys Val Thr Cys Ser Val
        35                  40                  45
Arg Gln Ser Ser Ala Gln Asn Arg Lys Tyr Thr Ile Lys Val Glu Val
    50                  55                  60
Pro Lys Val Ala Thr Gln Thr Val Gly Gly Val Glu Leu Pro Val Ala
65                  70                  75                  80
Ala Trp Arg Ser Tyr Leu Asn Leu Glu Leu Thr Ile Pro Ile Phe Ala
                85                  90                  95
Thr Asn Ser Asp Cys Glu Leu Ile Val Lys Ala Met Gln Gly Leu Leu
            100                 105                 110
Lys Asp Gly Asn Pro Ile Pro Ser Ala Ile Ala Ala Asn Ser Gly Ile
        115                 120                 125
```

Tyr

<210> SEQ ID NO 15
<211> LENGTH: 128
<212> TYPE: PRT
<213> ORGANISM: Bacteriophage PP7

<400> SEQUENCE: 15

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125

<210> SEQ ID NO 16
<211> LENGTH: 131
<212> TYPE: PRT
<213> ORGANISM: Bacteriophage AP205

<400> SEQUENCE: 16

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 17
<211> LENGTH: 132
<212> TYPE: PRT
<213> ORGANISM: Bacteriophage Qbeta

<400> SEQUENCE: 17

Ala Lys Leu Glu Thr Val Thr Leu Gly Asn Ile Gly Arg Asp Gly Lys
1               5                   10                  15

-continued

```
Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 18
<211> LENGTH: 132
<212> TYPE: PRT
<213> ORGANISM: Bacteriophage Qbeta

<400> SEQUENCE: 18

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 19
<211> LENGTH: 132
<212> TYPE: PRT
<213> ORGANISM: Bacteriophage Qbeta

<400> SEQUENCE: 19

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60
```

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
        130

<210> SEQ ID NO 20
<211> LENGTH: 132
<212> TYPE: PRT
<213> ORGANISM: Bacteriophage Qbeta

<400> SEQUENCE: 20

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
        130

<210> SEQ ID NO 21
<211> LENGTH: 132
<212> TYPE: PRT
<213> ORGANISM: Bacteriophage Qbeta

<400> SEQUENCE: 21

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
    130

<210> SEQ ID NO 22
<211> LENGTH: 131
<212> TYPE: PRT
<213> ORGANISM: Bacteriophage AP205

<400> SEQUENCE: 22

Met Ala Asn Lys Thr Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 23
<211> LENGTH: 131
<212> TYPE: PRT
<213> ORGANISM: Bacteriophage AP205

<400> SEQUENCE: 23

Met Ala Asn Lys Pro Met Gln Pro Ile Thr Ser Thr Ala Asp Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

SCALABLE PROCESS FOR PROTEIN PURIFICATION

FIELD OF THE INVENTION

This invention is related to the field protein purification. Provided is a process for the preparative purification of recombinantly expressed, self-assembled virus-like-particles (VLPs) from bacterial homogenates, wherein the process can be scaled up to a commercial production scale and wherein the process allows for efficient removal of endotoxin contaminations and other host cell derived impurities from the VLP preparation.

BACKGROUND OF THE INVENTION

Recent vaccination strategies exploit the immunogenicity of viruses or virus-like-particles (VLPs) to enhance the immune response towards antigens. For example, WO02/056905 demonstrates the utility of VLPs as carriers to present antigens linked thereto in highly ordered repetitive antigen arrays. Such antigen arrays can cause a strong immune response, in particular antibody responses, against the antigen, including self antigens. Furthermore, VLPs have been shown to be useful in the therapy of diseases as delivery means for immunostimulatory substances (WO2003/024481). VLPs are therefore useful in the production of pharmaceuticals for the treatment of infectious diseases and allergies as well as for the efficient induction of self-specific immune responses, e.g. for the treatment of cancer, rheumatoid arthritis and various other diseases. For the production of VLP based pharmaceuticals efficient processes for expression and purification of VLPs are required.

For reasons of scalability and efficiency and, thus, cost saving, VLP carriers for the manufacture of pharmaceuticals are preferably produced by recombinant gene expression in a prokaryotic expression system. Viral capsid proteins have been shown to efficiently self-assemble to form VLPs upon expression in a bacterial host. For example, hepatitis B virus derived VLP has been obtained by expression of HBc protein in *E. coli* and purification of the VLP from bacterial homogenate on a sucrose gradient (WO01/85208). VLPs of bacteriophages, preferably of RNA bacteriophages, are particularly suited as antigen carriers and have been produced in *E. coli*, wherein the assembled VLPs were isolated from crude bacterial homogenates by various methods.

For example, recombinant VLP derived from bacteriophage fr was isolated from lysed *E. coli* cells by ammonium sulphate precipitation followed by size exclusion chromatography using a Sephadex G100 column with a Sephadex G25 pre-column (Pushko et al. 1993, Protein Engineering 6(8) 883-891). Soluble recombinant VLPs derived from bacteriophage MS-2 were isolated from lysed *E. coli* cells by a combination of ammonium sulphate precipitation and separation on a sucrose density gradient, while less soluble variants were isolated by size exclusion chromatography (Mastico et al. 1993, Journal of General Virology 74:541-548). WO92/13081 teaches the isolation of MS-2 derived VLP by fractionated ammonium sulphate precipitation combined with either sucrose density gradient separation, gel filtration or immuno affinity chromatography. A multi step purification scheme for recombinant MS-2 derived VLP comprising ammonium sulphate precipitation, isoelectric point precipitation, sucrose density gradient separation and size exclusion chromatography was also reported (Stockley & Mastico 2000, Methods in Enzymology 326:551-569). Recombinant VLPs derived from bacteriophage Qβ have been purified from bacterial homogenate by size exclusion chromatography using a Sepharose column (Kozlovska et al. 1993, Gene 137:133-137) or by a combination of fractionated ammonium sulphate precipitation and size exclusion chromatography with Sepharose CL-4B (Vasiljeva et al 1998, FEBS Letters 431:7-11; Ciliens et al. 2000, FEBS Letters 24171:1-4).

Proteins isolated from bacterial homogenates are typically contaminated with endotoxins and other host cell derived impurities, such as host cell DNA and host cell proteins. The presence of host cell derived impurities, especially endotoxins, is generally undesired in pharmaceutical preparations. Endotoxins are lipopolysaccharides which are invariably associated with the outer membrane of gram-negative bacteria, such as *E. coli*. They show a strong toxic, inflammatory and/or immunogenic effect on mammals, including humans, when entering the blood stream. Thus, removal of even minute amounts of endotoxins from protein preparations used for the manufacture of a pharmaceutical composition is essential. The processes which so far have been applied for the purification of recombinant VLPs from bacterial homogenates are not capable of reliably removing endotoxin contaminants to an extent which is acceptable for pharmaceutical compositions and/or said processes comprise steps, such as sucrose gradient separation, which can hardly be scaled up for commercial production of the VLP.

It is an object of the present invention to provide a process for the purification of recombinantly expressed, self-assembled VLPs from bacterial homogenate, wherein the VLPs are essentially free of host cell derived impurities, especially of endotoxins, and wherein the process can be scaled up to a commercial production scale in a cost effective manner.

The assembly of the VLP takes place in the cytosol of the bacterial host expressing the VLP, while endotoxins are associated with the cell wall of the bacterial host. Therefore, endotoxins are typically not encapsulated inside the VLP and can thus be efficiently removed by the process of the invention. The VLP preparations obtained by the process of the invention typically comprise endotoxin contaminations at concentrations which are about 50 times lower than those observed in preparations obtained by the methods mentioned above.

The invention therefore provides a process for the purification of a VLP from a recombinant bacterial host expressing said VLP, wherein the process is capable of removing endotoxins and that fraction of nucleic acids and host cell proteins which is not encapsulated inside the VLP.

SUMMARY OF THE INVENTION

One embodiment of the invention is a process for the purification of a VLP from a recombinant bacterial host expressing said VLP, the process comprising a first chromatography using a first chromatography matrix, preferably a hydroxyapatite matrix or an anion exchange matrix, a second chromatography using a second chromatography matrix, preferably a hydroxyapatite matrix, and, optionally, a final purification step, also referred to as "polishing step", comprising at least one third chromatography, wherein preferably said at least one third chromatography is size exclusion chromatography. It has surprisingly been found that the combination of said first and said second chromatography provides for high purity VLP preparations, in particular for very efficient removal of endotoxins, wherein scalability of the process is maintained. It has further been found, that the removal of said endotoxins is most efficient, when said second chromatography matrix is a hydroxyapatite matrix.

One embodiment of the invention is a process for the purification of a VLP from a recombinant bacterial host expressing said VLP, the process comprising the steps of: (a) homogenizing said bacterial host; (b) clarifying the homogenate obtained by said homogenizing; (c) purifying said VLP from the clarified homogenate obtained by said clarifying in a first chromatography comprising the steps of: (i) binding said VLP to a first chromatography matrix; (ii) washing said first chromatography matrix; and (iii) eluting said VLP from said first chromatography matrix; and (d) further purifying said VLP from the eluate obtained by said first chromatography in a second chromatography, wherein said second chromatography is performed on a second chromatography matrix, wherein said second chromatography matrix is a hydroxyapatite matrix; wherein said steps are performed in the given order.

In a further embodiment said second chromatography comprises the steps of: (i) binding said VLP to said second chromatography matrix, wherein said second chromatography matrix is a hydroxyapatite matrix; (ii) washing said second chromatography matrix; and (iii) eluting said VLP from said second chromatography matrix; wherein said steps are performed in the given order.

In a further embodiment said process additionally comprising the step of finally purifying said VLP obtained by said second chromatography by at least one third chromatography, wherein said at least one third chromatography is selected from: (a) hydrophobic interaction chromatography (HIC); (b) immobilized metal ions affinity chromatography (IMAC); and (c) size exclusion chromatography.

In a further embodiment said VLP comprises capsid protein of a virus selected from the group consisting of: (a) RNA bacteriophage; (b) bacteriophage; (c) Hepatitis B virus; (d) measles virus; (e) Sindbis virus; (f) rotavirus; (g) foot-and-mouth-disease virus; (h) Norwalk virus; (i) Alpha Virus; (j) retrovirus; (k) retrotransposon Ty; (l) human Papilloma virus; (m) Polyoma virus; (n) Tobacco mosaic virus; and (o) Flock House Virus.

In a further embodiment said clarifying of said homogenate is performed by a method selected from the group consisting of: (a) centrifugation; (c) tangential flow filtration, preferably using a filter having a membrane comprising a pore size of about 0.45 μm; and (c) a combination of (a) and (c).

In a further embodiment said first chromatography matrix is an anion exchange matrix, preferably an anion exchange matrix comprising TMAE groups.

In a further embodiment said first chromatography matrix is a tentacle anion exchange matrix comprising (i) resin particles of cross-linked methacrylate polymer or cross-linked vinyl polymer (ii) acrylamide tentacles, wherein said acrylamide tentacles are attached to the surface of said resin particles, and wherein said acrylamide tentacles are substituted with TMAE (Trimethylaminoethyl-) groups.

In a further embodiment said first chromatography matrix is selected from the group consisting of: (a) Fractogel® EMD TMAE (M), preferably having a particle size of 40-90 μm; (b) Fractogel® EMD TMAE Hicap (M), preferably having a particle size of 40-90 μm; (c) Fractoprep® DEAE, preferably having a particle size of 30-150 μm; (d) Macro-Prep® CHT Ceramic Hydroxyapatite Type I, preferably having a particle size of about 80 μm; (e) Macro-Prep® CHT Ceramic Hydroxyapatite Type II, preferably having a particle size of about 80 μm; (f) Matrex® Granular Silica PEI-300 Å, preferably having a particle size of 35-70 μm; (g) Matrex® Granular Silica PEI-1000 Å, preferably having a particle size of 35-70 μm; (h) Poros 50 HQ; (i) CIM-QA (quarternary amino group, BIA Separations Cat. No. 210.5113), and (j) CIM-DEAE.

In a further embodiment said first chromatography comprises the steps of: (i) equilibrating said first chromatography matrix with a first equilibration buffer; (ii) binding said VLP to a first chromatography matrix; (iii) washing said first chromatography matrix with a first washing buffer; and (iv) eluting said VLP from said first chromatography matrix with a first elution puffer; wherein said first equilibration buffer, said first washing buffer and said first elution buffer comprise an inorganic salt, preferably an alkaline metal halogenide, more preferably potassium chloride or sodium chloride, most preferably sodium chloride.

In a further embodiment said first equilibration buffer comprises at most about 200 mM sodium chloride, said first washing buffer comprises about 425 mM sodium chloride, and said first elution buffer comprises least about 500 mM sodium chloride or a gradient of sodium chloride, wherein preferably said gradient is from at most about 400 to at least about 650 mM sodium chloride, preferably from 425 to 650 mM sodium chloride.

In a further embodiment said first equilibration buffer, said first washing buffer and said first elution buffer comprise a pH of about 7.2, wherein preferably said pH is stabilized by a phosphate buffer, more preferably by about 20 mM phosphate buffer, most preferably by about 20 mM sodium phosphate buffer.

In a further embodiment said hydroxyapatite matrix is a ceramic hydroxyapatite matrix, wherein preferably said ceramic hydroxyapatite matrix comprises a particle size of about 80 μm and a pore size of the particles of about 800-1000 Å, wherein further preferably said ceramic hydroxyapatite matrix is Macro-Prep® CHT Ceramic Hydroxyapatite Type II.

In a further embodiment said second chromatography comprises the steps of: (i) equilibrating said second chromatography matrix with a second equilibration buffer; (ii) binding said VLP to said second chromatography matrix, wherein said second chromatography matrix is a hydroxyapatite matrix; (ii) washing said second chromatography matrix with a second washing buffer; and (iii) eluting said VLP from said second chromatography matrix; wherein said second equilibration buffer, said second washing buffer and said second elution buffer, comprise an inorganic salt, preferably an alkaline metal halogenide, more preferably potassium chloride or sodium chloride, most preferably sodium chloride.

In a further embodiment said second equilibration buffer comprises about 100 to 400 mM sodium chloride, said second washing buffer comprises about 150 mM sodium chloride, and said second elution buffer comprises 900 mM sodium chloride and about 200 mM sodium phosphate buffer.

In a further embodiment said second equilibration buffer, said second washing buffer and said second elution buffer comprise a pH of about 7.2, wherein preferably said pH is stabilized by a phosphate buffer, preferably by a sodium phosphate buffer.

In a further embodiment said clarifying further comprises the step of exposing said VLP to oxidative conditions.

In a further embodiment said least one third chromatography is at least one, preferably exactly one, size exclusion chromatography, wherein said size exclusion chromatography is preferably performed using a gel filtration matrix selected from the group consisting of: (a) Sephadex G-25; (b) Sepharose CL-4B; and (c) Sephacryl-S400.

In a further embodiment the invention provides a process for the purification of a VLP of RNA bacteriophage Qβ from a recombinant bacterial host expressing said VLP, the process comprising the steps of: (a) homogenizing said bacterial host; (b) clarifying the homogenate obtained by said homogenizing, wherein said clarifying further comprises the step of exposing said VLP to oxidative conditions; (c) purifying said VLP from the clarified homogenate obtained by said clarifying in a first chromatography comprising the steps of: (i) equilibrating a tentacle anion exchange matrix, wherein said equilibrating is performed with a first equilibration buffer, wherein said first equilibration buffer comprises about 150 mM sodium chloride and a pH of 7.2; (ii) binding said VLP to said tentacle anion exchange matrix; (iii) washing said tentacle anion exchange matrix, wherein said washing is performed with a first washing buffer comprising about 425 mM sodium chloride and a pH of 7.2; and (iv) eluting said VLP from said tentacle anion exchange matrix, wherein said eluting is performed with a first elution buffer comprising a gradient of 425 to 650 mM sodium chloride and a pH of 7.2; wherein preferably said tentacle anion exchange matrix is a tentacle anion exchange matrix as defined above, most preferably Fractogel® EMD TMAE (M); (d) further purifying said VLP from the eluate obtained by said first chromatography in a second chromatography comprising the steps of: (i) equilibrating a hydroxyapatite matrix wherein said equilibrating is performed with a second equilibration buffer comprising about 150 mM sodium chloride and a pH of 7.2; (ii) binding said VLP to hydroxyapatite matrix, preferably in the presence of about 250 mM sodium chloride; (iii) washing said hydroxyapatite matrix, wherein said washing is performed with a second washing buffer comprising about 150 mM sodium chloride and a pH of 7.2; (iv) eluting said VLP from said hydroxyapatite matrix, wherein said eluting is performed with a second elution buffer comprising about 900 mM sodium chloride, about 200 mM sodium phosphate buffer and a pH of 7.2; wherein preferably said hydroxyapatite matrix is a hydroxyapatite matrix as defined above, most preferably a Macro-Prep® CHT Ceramic Hydroxyapatite Type II matrix; (e) finally purifying said VLP contained in the eluate of said second chromatography by exactly one size exclusion chromatography, wherein said size exclusion chromatography is performed in the presence of about 150 mM sodium chloride, and wherein further said size exclusion chromatography is performed using a Sepharose CL-4B gel filtration matrix; wherein said steps are performed in the given order.

In a further embodiment the invention provides a process for the purification of a VLP of RNA bacteriophage AP205 from a recombinant bacterial host expressing said VLP, the process comprising the steps of: (a) homogenizing said bacterial host; (b) clarifying the homogenate obtained by said homogenizing, wherein said clarifying further comprises the step of exposing said VLP to oxidative conditions; (c) purifying said VLP from the clarified homogenate obtained by said clarifying in a first chromatography comprising the steps of: (i) equilibrating a tentacle anion exchange matrix, wherein said equilibrating is performed with a first equilibration buffer, wherein said first equilibration buffer comprises about 150 mM sodium chloride and a pH of 7.2; (ii) binding said tentacle anion exchange matrix; (iii) washing said tentacle anion exchange matrix, wherein said washing is performed with a first washing buffer comprising about 425 mM sodium chloride and a pH of 7.2; and (iv) eluting said VLP from said tentacle anion exchange matrix, wherein said eluting is performed with a first elution buffer comprising about 550 mM sodium chloride and a pH of 7.2; wherein preferably said tentacle anion exchange matrix is a tentacle anion exchange matrix as defined above, most preferably Fractogel® EMD TMAE (M); (d) further purifying said VLP from the eluate obtained by said first chromatography in a second chromatography comprising the steps of: (i) equilibrating a hydroxyapatite matrix, wherein said equilibrating is performed with a second equilibration buffer comprising, about 100 mM sodium chloride and about 5 mM sodium phosphate buffer and a pH of 7.2; (ii) binding said VLP to said hydroxyapatite matrix, preferably in the presence of about 100 mM sodium chloride and about 5 mM sodium phosphate buffer; (iii) washing said hydroxyapatite matrix wherein said washing is performed with a second washing buffer comprising about 100 mM sodium chloride, about 5 mM sodium phosphate buffer and a pH of 7.2; (iv) eluting said VLP from said hydroxyapatite matrix, wherein said eluting is performed with a second elution buffer comprising about 250 mM sodium chloride, about 50 mM sodium phosphate buffer and a pH of 7.2; wherein preferably said hydroxyapatite matrix is a hydroxyapatite matrix as defined above, most preferably a Macro-Prep® CHT Ceramic Hydroxyapatite Type II matrix; (e) finally purifying said VLP contained in the eluate of said second chromatography by exactly one size exclusion chromatography, wherein said size exclusion chromatography is performed in the presence of about 150 mM sodium chloride, and wherein further said size exclusion chromatography is performed using a Sepharose CL-4B gel filtration matrix; wherein said steps are performed in the given order.

DETAILED DESCRIPTION OF THE INVENTION

Unless defined otherwise, all technical and scientific terms used herein have the same meanings as commonly understood by one of ordinary skill in the art to which this invention belongs.

"one", "a", or "an": When the terms "one", "a", or "an" are used in this disclosure, they mean "at least one" or "one or more", unless otherwise indicated.

"About": The term "about" as used herein in connection with a numerical value refers to a range of ±10% of said value. E.g. a concentration of about 100 mM refers to a range of concentration of 100 mM±10%, i.e. 90 to 110 mM; a concentration of at least about 100 mM refers to a concentration which is not below 90 mM.

"Homogenate": The term "homogenate" of a bacterial host relates to a suspension of bacteria cells, wherein at least 50%, preferably at least 75%, more preferably at least 90%, still more preferably at least 95%, most preferably at least 99% of the bacteria cells have been disrupted by physical and/or enzymatic means. Disruption of the bacteria cells can, for example, be achieved by sonication, by passage through a high pressure liquid homogenizer like the APV LAB 1000, by passage through a French press, by grinding with aluminium oxide and/or by lysozyme treatment.

"Coat protein"/"capsid protein": The term "coat protein" and the interchangeably used term "capsid protein" within this application refers to a viral protein, preferably a subunit of a natural capsid of a virus, preferably a RNA bacteriophage, which is capable of being incorporated into a virus capsid or a VLP. For example, the specific gene product of the coat protein gene of RNA bacteriophage Qβ is referred to as "Qβ CP", whereas the "coat proteins" or "capsid proteins" of bacteriophage Qβ comprise the "Qβ CP" as well as the A1 protein.

"Fragment of a protein": The term "fragment of a protein", in particular fragment of a recombinant protein or recombinant capsid protein, as used herein, is defined as a polypeptide, which is of at least 70%, preferably at least 80%, more preferably at least 90%, even more preferably at least 95% the length of the wild-type recombinant protein, or capsid protein, respectively and which preferably retains the capability of forming VLP. Preferably the fragment is obtained by at least one internal deletion, at least one truncation or at least one combination thereof. The term "fragment of a recombinant protein" or "fragment of a capsid protein" shall further encompass polypeptide, which has at least 80%, preferably 90%, even more preferably 95% amino acid sequence identity with the "fragment of a recombinant protein" or "fragment of a coat protein", respectively, as defined above and which is preferably capable of assembling into a virus-like particle.

"Mutant recombinant protein"/"mutant of a recombinant protein": The terms "mutant recombinant protein" and "mutant of a recombinant protein" as interchangeably used in this application, or the terms "mutant coat protein" and "mutant of a coat protein", as interchangeably used in this application, refer to a polypeptide having an amino acid sequence derived from the wild type recombinant protein, or coat protein, respectively, wherein the amino acid sequence is at least 80%, preferably at least 85%, 90%, 95%, 97%, or 99% identical to the wild type sequence and preferably retains the ability to assemble into a VLP.

"Polypeptide": As used herein the term "polypeptide" refers to a polymer composed of amino acid residues, generally natural amino acid residues, linked together through peptide bonds. Although a polypeptide may not necessarily be limited in size, the term polypeptide is often used in conjunction with peptide of a size of about ten to about 50 amino acids.

"Protein": As used herein, the term protein refers to a polypeptide generally of a size of above 20, more particularly of above 50 amino acid residues. Proteins generally have a defined three dimensional structure although they do not necessarily need to, and are often referred to as folded, in opposition to peptides and polypeptides which often do not possess a defined three-dimensional structure, but rather can adopt a large number of different conformations, and are referred to as unfolded. The defined three-dimensional structures of proteins is especially important for the association between the core particle and the antigen, mediated by the second attachment site, and in particular by way of chemical cross-linking between the first and second attachment site using a chemical cross-linker. The amino acid linker is also intimately related to the structural properties of proteins in some aspects of the invention.

"Recombinant coat protein"/"recombinant capsid protein": A capsid protein which is synthesised by a recombinant host cell.

"Recombinant bacterial host": As used herein, the term "recombinant bacterial host" refers to a bacteria cell, preferably an *E. coli* cell, into which one or more nucleic acid molecules encoding have been introduced, wherein said nucleic acid molecule or nucleic acid molecules encode a capsid protein forming the VLP to be purified by the process of the invention.

"Recombinant VLP": The term "recombinant VLP", as used herein, refers to a VLP that is obtained by a process which comprises at least one step of recombinant DNA technology. The term "VLP recombinantly produced", as used herein, refers to a VLP that is obtained by a process which comprises at least one step of recombinant DNA technology. Thus, the terms "recombinant VLP" and "VLP recombinantly produced" are interchangeably used herein and should have the identical meaning.

"RNA bacteriophage": As used herein, the term "RNA bacteriophage" refers to an RNA virus infecting bacteria, preferably to single-stranded positive-sense RNA viruses infecting bacteria.

"Sequence identity": The amino acid sequence identity of polypeptides can be determined conventionally using known computer programs such as the Bestfit program. When using Bestfit or any other sequence alignment program, preferably using Bestfit, to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, polypeptides or a fragment thereof disclosed in this invention.

"Tentacle anion exchange matrix": The expressions "tentacle anion exchange matrix" as used herein refers to an anion exchange matrix implementing the tentacle technology typically and preferably as disclosed in WO96/22316, WO97/49754, EP0337144, DE4334359 or WO95/09695. Anion exchange matrices implementing the tentacle technology are resin particles comprising, preferably on their surface, spacers formed by linear polymer chains (tentacles), wherein said tentacles are substituted with functional groups having anion exchange activity.

Preferred tentacle anion exchange matrices are based on resins of copolymers on a methacrylate basis or on resins of vinyl polymers. Specifically preferred tentacle ion exchange matrices are Fractogel® EMD TMAE ion exchangers and Fractoprep® DEAE ion exchangers (Merck), the most preferred tentacle anion exchange matrix is Fractogel® ion EMD TMAE.

"Virus-like particle (VLP)": as used herein, the term "virus-like particle" refers to a structure resembling a virus particle or it refers to a non-replicative or non-infectious, preferably a non-replicative and non-infectious virus particle, or it refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. Preferably a virus-like particle in accordance with the invention is non-replicative and/or non-infectious since it lacks all or part of the viral genome or genome function. Typically, a virus-like particle lacks all or part of the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, preferably RNA bacteriophage. The terms "viral capsid" or "capsid", refer to a macromolecular assembly composed of viral protein subunits. Typically, there are 60, 120, 180, 240, 300, 360 and more than 360 viral protein subunits. Typically and preferably, the interactions of these subunits lead to the formation of viral capsid or viral-capsid like structure with an inherent repetitive organization, wherein said structure is, typically, spherical or tubular. For example, the capsids of RNA bacteriophages or HBcAgs have a spherical form of icosahedral symmetry.

"Virus-like particle of a RNA bacteriophage": As used herein, the term "virus-like particle of a RNA bacteriophage"

refers to a virus-like particle comprising, or preferably consisting essentially of or consisting of coat proteins, mutants or fragments thereof, of a RNA bacteriophage. In addition, virus-like particle of a RNA bacteriophage resembling the structure of a RNA bacteriophage, being non replicative and/or non-infectious, and lacking at least the gene or genes encoding for the replication machinery of the RNA bacteriophage, and typically also lacking the gene or genes encoding the protein or proteins responsible for viral attachment to or entry into the host. Preferred VLPs derived from RNA bacteriophages exhibit icosahedral symmetry and consist of 180 subunits. Within this present disclosure the term "subunit" and "monomer" are interchangeably and equivalently used within this context. In this application, the term "RNA bacteriophage" and the term "RNA-bacteriophage" are interchangeably used. A preferred method to render a virus-like particle of a RNA bacteriophage non replicative and/or non-infectious is by genetic manipulation.

The invention relates to a process for the purification of self-assembled virus-like particles (VLPs) from a homogenate of a bacterial host, wherein said VLPs were produced by expression of one or more viral capsid proteins in said bacterial host. VLPs derived from any virus known in the art may be purified by the process of the invention. Illustrative DNA or RNA viruses, the coat or capsid protein of which can be used for the preparation of VLPs have been disclosed in WO 2004/009124 on page 25, line 10-21, on page 26, line 11-28, and on page 28, line 4 to page 31, line 4. Almost all commonly known viruses have been sequenced and the genes encoding their coat proteins are available to the artisan. The preparation of VLPs by recombinantly expressing viral coat protein in a host is within the common knowledge of a skilled artisan.

One embodiment of the invention is a process for the purification of a VLP from a recombinant bacterial host expressing said VLP, the process comprising the steps of: (a) homogenizing said bacterial host; (b) clarifying the homogenate obtained by said homogenizing; (c) purifying said VLP from the clarified homogenate obtained by said clarifying in a first chromatography comprising the steps of: (i) binding said VLP to a first chromatography matrix; (ii) washing said first chromatography matrix; and (iii) eluting said VLP from said first chromatography matrix; and (d) further purifying said VLP from the eluate obtained by said first chromatography in a second chromatography, wherein said second chromatography is performed on a second chromatography matrix, wherein said second chromatography matrix is a hydroxyapatite matrix; wherein said steps are performed in the given order.

In a preferred embodiment said second chromatography is a subtractive chromatography, wherein contaminants are bound to said second chromatography matrix in the presence of an inorganic salt, and wherein the concentration of said inorganic salt prevents the binding of said VLP to said second chromatography matrix. In a further preferred embodiment said second chromatography is a subtractive chromatography, wherein preferably said second chromatography matrix is a hydroxyapatite matrix, and wherein further preferably said inorganic salt is an alkaline metal halogenide, preferably potassium chloride or sodium chloride, most preferably sodium chloride, and wherein further preferably the concentration of said inorganic salt is at least about 400 mM.

A further embodiment of the invention is a process for the purification of a VLP from a recombinant bacterial host expressing said VLP, the process comprising the steps of: (a) homogenizing said bacterial host; (b) clarifying the homogenate obtained by said homogenizing; (c) purifying said VLP from the clarified homogenate obtained by said clarifying in a first chromatography comprising the steps of: (i) binding said VLP to a first chromatography matrix; (ii) washing said first chromatography matrix; and (iii) eluting said VLP from said first chromatography matrix; and (d) further purifying said VLP from the eluate obtained by said first chromatography in a second chromatography comprising the steps of: (i) binding said VLP to a second chromatography matrix, wherein preferably said second chromatography matrix is a hydroxyapatite matrix; (ii) washing said second chromatography matrix; and (iii) eluting said VLP from said second chromatography matrix; wherein said steps are performed in the given order.

In one embodiment, said VLP comprises, or alternatively essentially consists of, or consists of, recombinant proteins, mutants or fragments thereof, of a virus, wherein said virus preferably is a RNA virus, more preferably a single stranded RNA virus, still more preferably a single stranded positive sense RNA virus, most preferably a RNA bacteriophage.

In a further embodiment, said VLP comprises, or alternatively essentially consists of, or consists of, recombinant proteins, mutants or fragments thereof, of a virus selected form the group consisting of: (a) RNA bacteriophages; (b) bacteriophages; (c) Hepatitis B virus, preferably its capsid protein (Ulrich, et al., Virus Res. 50:141-182 (1998)) or its surface protein (WO 92/11291); (d) measles virus (Warnes, et al., Gene 160:173-178 (1995)); (e) Sindbis virus; (f) rotavirus (U.S. Pat. Nos. 5,071,651 and 5,374,426); (g) foot-and-mouth-disease virus (Twomey, et al., Vaccine 13:1603 1610, (1995)); (h) Norwalk virus (Jiang, X., et al., Science 250: 1580 1583 (1990); Matsui, S. M., et al., J. Clin. Invest. 87:1456 1461 (1991)); (i) Alphavirus; (j) retrovirus, preferably its GAG protein (WO 96/30523); (k) retrotransposon Ty, preferably the protein p1; (l) human Papilloma virus (WO 98/15631); (m) Polyoma virus; (n) Tobacco mosaic virus; (o) Flock House Virus, (p) cowpea mosaic virus (CPMV), (q) cowpea chlorotic mottle virus (CCMV), and a virus of the genus *Sobemovirus*.

In one preferred embodiment, said VLP comprises, or alternatively essentially consists of, or consists of more than one amino acid sequence, preferably two amino acid sequences, of the recombinant proteins, mutants or fragments thereof (referred to as mosaic VLP).

In a further preferred embodiment, said VLP is a VLP of Hepatitis B virus. The preparation of Hepatitis B virus-like particles has been disclosed, inter alia, in WO00/32227, WO01/85208 and in WO02/056905. In a preferred embodiment the VLP is composed of HBcAg (SEQ ID NO:1). Other variants of HBcAg suitable for use in the practice of the present invention have been disclosed in page 34-39 of WO01/056905. In a further preferred embodiment of the invention, a lysine residue is introduced into the HBcAg polypeptide, to mediate the linking of an antigen to the VLP of HBcAg. In preferred embodiments, VLPs and compositions of the invention are prepared using a HBcAg comprising, or alternatively essentially consisting of, or consisting of amino acids 1-144, or 1-149, 1-185 of SEQ ID NO:1, which is modified so that the amino acids at positions 79 and 80 are replaced with a peptide having the amino acid sequence of Gly-Gly-Lys-Gly-Gly. This modification changes the SEQ ID NO:1 to SEQ ID NO:2. In further preferred embodiments, the cysteine residues at positions 48 and 110 of SEQ ID NO:2, or its corresponding fragments, preferably 1-144 or 1-149, are mutated to serine. The invention further relates to the purification of VLPs comprising or alternatively consisting of Hepatitis B core protein mutants having above noted corresponding amino acid alterations. The invention further includes VLPs, comprising HBcAg polypeptides which comprise, or alternatively consist of, amino acid sequences which are at least 80%, 85%, 90%, 95%, 97% or 99% identical to SEQ ID NO:2.

In one preferred embodiment of the invention, the virus-like particle comprises, consists essentially of, or alternatively consists of, recombinant coat proteins, mutants or fragments thereof, of a RNA bacteriophage, wherein preferably, said RNA bacteriophage is selected from the group consisting of (a) bacteriophage BZ13, (b) bacteriophage GA, (c) bacteriophage JP34, (d) bacteriophage KU1, (d) bacteriophage TH1, (e) bacteriophage MS2, (f) bacteriophage f2, (g) bacteriophage fr, (h) bacteriophage JP501, (i) bacteriophage M12, (j) bacteriophage R17, (k) bacteriophage PP7, (l) bacteriophage FI, (m) bacteriophage ID2, (n) bacteriophage NL95, (o) bacteriophage SP, (p) bacteriophage TW28, (q) bacteriophage Qβ, (r) bacteriophage M11, (s) bacteriophage MX1, (t) bacteriophage ST, (u) bacteriophage TW18, and (v) bacteriophage VK. In a further preferred embodiment said RNA bacteriophage is selected from the group consisting of: (a) bacteriophage Qβ, (b) bacteriophage R17, (c) bacteriophage fr, (d) bacteriophage GA, (e) bacteriophage SP, (f) bacteriophage MS2, (g) bacteriophage M11, (h) bacteriophage MX1, (i) bacteriophage NL95, (k) bacteriophage f2, (l) bacteriophage PP7, and (m) bacteriophage AP205.

In a further preferred embodiment said RNA bacteriophage is selected from the group consisting of: (a) bacteriophage Qβ; (b) bacteriophage R17; (c) bacteriophage fr; (d) bacteriophage GA; (e) bacteriophage SP; (f) bacteriophage MS2; (g) bacteriophage M11; (h) bacteriophage MX1; (i) bacteriophage NL95; (j) bacteriophage f2; (k) bacteriophage PP7 and (l) bacteriophage AP205.

In one preferred embodiment said VLP comprises coat protein, mutants or fragments thereof, of RNA bacteriophages, wherein preferably said coat protein has an amino acid sequence selected from the group consisting of: (a) SEQ ID NO:3 referring to Qβ CP; (b) a mixture of SEQ ID NO:3 and SEQ ID NO:4 (Qβ A1 protein); (c) SEQ ID NO:5 (R17 capsid protein); (d) SEQ ID NO:6 (fr capsid protein); (e) SEQ ID NO:7 (GA capsid protein); (f) SEQ ID NO:8 (SP capsid protein); (g) a mixture of SEQ ID NO:8 and SEQ ID NO:9; (h) SEQ ID NO:10 (MS2 capsid protein); (i) SEQ ID NO:11 (M11 capsid protein); (j) SEQ ID NO:12 (MX1 capsid protein); (k) SEQ ID NO:13 (NL95 capsid protein); (l) SEQ ID NO:14 (f2 capsid protein); (m) SEQ ID NO:15 (PP7 capsid protein); and (n) SEQ ID NO:16 (AP205 capsid protein).

In one preferred embodiment of the invention, said VLP is a mosaic VLP comprising or alternatively consisting of more than one amino acid sequence, preferably two amino acid sequences, of coat proteins, mutants or fragments thereof, of a RNA bacteriophage. In one very preferred embodiment, said VLP comprises or alternatively consists of two different coat proteins of a RNA bacteriophage, said two coat proteins have an amino acid sequence of SEQ ID NO:3 and SEQ ID NO:4, or of SEQ ID NO:8 and SEQ ID NO:9. In preferred embodiments of the present invention, said VLP comprises, or alternatively consists essentially of, or alternatively consists of recombinant coat proteins, mutants or fragments thereof, of the RNA-bacteriophage Qβ, fr, AP205 or GA.

In one preferred embodiment, said VLP is a VLP of RNA bacteriophage Qβ. The capsid or virus-like particle of Qβ shows an icosahedral phage-like capsid structure with a diameter of 25 nm and T=3 quasi symmetry. The capsid contains 180 copies of the coat protein, which are linked in covalent pentamers and hexamers by disulfide bridges (Golmohammadi, R. et al., Structure 4:543-5554 (1996)), leading to a remarkable stability of the Qβ capsid. Capsids or VLPs made from recombinant Qβ coat protein may contain, however, subunits which are either not linked via disulfide bonds to other subunits within the capsid, or which are incompletely linked, meaning that they comprise less than the maximum number of possible disulfide bonds.

Further preferred virus-like particles of RNA bacteriophages, in particular of Qβ and fr in accordance of this invention are disclosed in WO 02/056905, the disclosure of which is herewith incorporated by reference in its entirety. Particular Example 18 of WO 02/056905 gave detailed description of preparation of VLP particles from Qβ.

Upon expression in E. coli, the N-terminal methionine of Qβ coat protein is usually removed (Stoll, E. et al., J. Biol. Chem. 252:990-993 (1977)). VLP composed of Qβ coat proteins where the N-terminal methionine has not been removed, or VLPs comprising a mixture of Qβ coat proteins where the N-terminal methionine is either cleaved or present are also within the scope of the present invention.

In another preferred embodiment, said VLP is a VLP of RNA bacteriophage AP205. Assembly-competent mutant forms of AP205 VLPs, including AP205 coat protein with the substitution of proline at amino acid 5 to threonine, may also be used in the practice of the invention and leads to other preferred embodiments of the invention. WO 2004/007538 describes, in particular in Example 1 and Example 2, how to obtain VLP comprising AP205 coat proteins, and hereby in particular the expression and the purification thereto.

In one preferred embodiment, said VLP comprises or alternatively essentially consists of, or consists of a mutant coat protein of a virus, preferably of a RNA bacteriophage, wherein said mutant coat protein has been modified by removal of at least one lysine residue by way of substitution and/or by way of deletion. In another preferred embodiment, said VLP comprises or alternatively essentially consists of, or consists of a mutant coat protein of a virus, preferably of a RNA bacteriophage, wherein said mutant coat protein has been modified by addition of at least one lysine residue by way of substitution and/or by way of insertion. The deletion, substitution or addition of at least one lysine residue allows varying the degree of coupling with an antigen.

VLPs or capsids of Qβ coat protein display a defined number of lysine residues on their surface, with a defined topology with three lysine residues pointing towards the interior of the capsid and interacting with the RNA, and four other lysine residues exposed to the exterior of the capsid. Preferably, the at least one first attachment site is a lysine residue, pointing to or being on the exterior of the VLP.

The purification of Qβ mutants, of which exposed lysine residues are replaced by arginines is also encompassed by the present invention. Preferably, these mutant coat proteins comprise or alternatively essentially consist of, or consist of an amino acid sequence selected from the group of (a) Qβ-240 (SEQ ID NO:17, Lys13→Arg); (b) Qβ-243 (SEQ ID NO:18, Asn10→Lys); (c) Qβ-250 (SEQ ID NO:19, Lys2→Arg); (d) Qβ-251 (SEQ ID NO:20, Lys16→Arg); and (e) Qβ-259 (SEQ ID NO:21, Lys2→Arg, Lys 16→Arg). The construction, expression and purification of the above indicated Qβ mutant coat proteins, mutant Qβ coat protein VLPs and capsids, respectively, are described in WO02/056905. In particular is hereby referred to Example 18 of above mentioned application.

In a further preferred embodiment said VLP comprises or alternatively essentially consists of, or consists of a capsid protein of bacteriophage AP205 having the amino acid sequence depicted in SEQ ID NO:16 or a mutation thereof, which is capable of forming a VLP, preferably the proteins AP205 P5T (SEQ ID NO:22) or AP205 N14D (SEQ ID NO:23).

In a very preferred embodiment said VLP comprises the 132 amino acid coat protein C of *E. coli* RNA bacteriophage Qβ having the amino acid sequence depicted in SEQ ID NO:3 (133 amino acids with methionine in position 1).

In a further preferred embodiment said VLP comprises a nucleic acid which is encapsulated inside said VLP, wherein preferably said nucleic acid is DNA or RNA, most preferably RNA, and wherein further preferably the amount of said nucleic acid, preferably of said RNA, is at least 5 µg, at least 10 µg, at least 20 µg, at least 30 µg at least 40 µg per 100 µg of capsid protein. In a further preferred embodiment said amount of said nucleic acid, preferably of said RNA, is 5 to 60 µg, more preferably 10 to 50 µg, still more preferably 20 to 40 µg, most preferably 25 to 35 µg per 100 µg of capsid protein.

In one embodiment, said bacterial host is an *E. coli* strain, preferably an *E. coli* strain selected from the group consisting of RB791, DH20, Y1088, W3110 and MG1655. Most preferably, said bacterial host is *E. coli* RB791.

In one embodiment the process of the invention is performed at a temperature of 0 to 10° C., preferably of 2 to 8° C., most preferably of about 5° C.

The process of the invention comprises the steps of (a) homogenizing said bacterial host; (b) clarifying the homogenate obtained by said homogenizing; (c) purifying said VLP from the clarified homogenate obtained by said clarifying in a first chromatography, (d) further purifying said VLP from the eluate obtained by said first chromatography in a second chromatography, and, optionally, (e) further purifying said VLP from the eluate of said second chromatography by at least one third chromatography, wherein preferably said at least one third chromatography is a size exclusion chromatography. In a preferred embodiment the steps of (a) homogenizing said bacterial host and (b) clarifying the homogenate obtained by said homogenizing are performed at a temperature of 0 to 10° C., preferably of 2 to 8° C., most preferably of about 5° C. In a further preferred embodiment said purifying of said VLP from the clarified homogenate, said further purifying of said VLP from the eluate obtained by said first chromatography, and/or said further purifying of said VLP contained in the eluate of said second chromatography are performed at room temperature, preferably at 15 to 35° C., more preferably at 18 to 26° C., still more preferably at 20 to 24° C., most preferably at 22° C.

The process of the invention comprises the step of homogenizing said bacterial host. Cells of said bacterial host are harvested, e.g. by centrifugation, and optionally stored at −80° C. Said homogenizing said bacterial host is performed by disrupting the cells of said bacterial host by physical, chemical or enzymatic means or by a combination thereof. Preferably said homogenizing is performed by disrupting the cell wall of said bacterial host by sonication, by passage through a high pressure liquid homogenizer like, for example, APV LAB 1000, by passage through a French press, or by grinding with aluminium oxide. Alternatively or additionally, preferably additionally, said homogenizing is performed by destabilizing the cell wall of said bacterial host by detergent, preferably by sodium dodecyl sulphate (SDS), or, more preferably, by non-ionic detergents, preferably selected from Triton® X-100, Triton® X-114, Tween® 20, Igepal® CA 630, Brij®35 and mixtures thereof. In a very preferred embodiment said detergent is Triton® X-100. Said detergent is preferably applied in a concentration of 0.01 to 30%, more preferably 0.01 to 5%, most preferably about 0.1%. Alternatively or additionally, said homogenizing is performed by destabilizing the cell wall of said bacterial host by exposure to a cell wall degrading enzyme, most preferably lysozyme.

The disruption of the bacteria cells is improved when the cell suspension is passed through a high pressure liquid homogenizer repeatedly. In a preferred embodiment said homogenizing said bacterial host is performed by passing said bacterial host through a high pressure liquid homogenizer at least once, preferably at least twice, more preferably at least three times, most preferably three times. The usage of a high pressure liquid homogenizer significantly improves the scalability of the process as it can be operated in a continuous mode. In a preferred embodiment, said homogenizing is performed by suspending said bacterial host in a suspension buffer and passing the suspension through a high pressure liquid homogenizer, preferably APV LAB 1000, at a pressure of 300 to 1200 bar, preferably 500 to 900 bar, more preferably 600 to 800 bar and most preferably about 700 bar. The time required for homogenization in continuous mode needs to be adapted to the volume and the cell density of the cell suspension. Criteria for sufficient homogenization of the bacterial host are the percentage of cells remaining intact as observed, for example, by microscopy, or the concentration of capsid protein detectable in the supernatant after centrifugation. Said suspension buffer preferably comprises an alkaline pH of about 8, an agent capable of forming complexes with metal ions, preferably EDTA, most preferably 1-50 mM EDTA, and a detergent, preferably selected from SDS, Tween-20 or Triton X-100, most preferably Triton X-100, wherein the concentration of the detergent is about 0.01 to 1.0%, more preferably about 0.05 to 0.5%, most preferably about 0.1%. In a very preferred embodiment said suspension buffer comprises a pH of 8.0, 5 mM EDTA and 0.1% (w/w) Triton X-100. In a further preferred embodiment said suspension buffer comprises a cell wall degrading enzyme, most preferably lysozyme.

The process of the invention further comprises the step of clarifying the homogenate obtained by said homogenizing, wherein i.e. cell debris is removed from the homogenate by either filtration or centrifugation. In one embodiment said homogenate is diluted before said clarifying is performed. In a preferred embodiment said clarifying is performed by filtering said homogenate in a tangential flow filtration (see Example 2), preferably by tangential flow filtration using a filter suitable for the processing of high viscosity media, preferably a filter cassette with an open channel configuration, wherein further preferably said filter, preferably said filter cassette with an open channel configuration, is equipped with a membrane having a pore size of 0.2 to 1.0 µm, preferably of 0.3 to 0.6 µm, more preferably of about 0.45 µm, most preferably 0.45 µm. In a further, equally preferred embodiment said clarifying is performed by centrifuging said homogenate (see Example 3), wherein preferably said homogenate is exposed to an acceleration of at least 7,000×g, more preferably at least 10,000×g for a period of time which is sufficient for the complete sedimentation of the cell debris. The required centrifugation time depends on the volume of the homogenate and the given technical set up. The artisan is able to determine the required centrifugation time empirically which is required to obtain a sufficiently solid pellet. Tangential flow filtration as well as centrifugation allow for efficient scale-up of the process. To obtain a clarified homogenate which is essentially free of cell debris it is advantageous to perform said clarifying of said homogenate by a combination of centrifugation and filtration. In a preferred embodiment said clarifying of said homogenate is achieved by a method selected from the group of (a) centrifuging said homogenate, (b) filtering said homogenate by tangential flow filtration, and (c) a combination of (a) and (b). In a very preferred embodiment said method is a combination of centrifuging said homogenate and filtering said homogenate by tangential flow filtration, wherein preferably first said homogenate is clarified by centrifuging said homogenate and second the supernatant obtained by said centrifuging is further clarified by filtering said supernatant by tangential flow filtration (see Example 3a). Optionally, said clarified homogenate is further clarified by sterile filtration to remove remaining cell debris and other particles. Therefore, in a further embodiment said clarifying further comprises the step of sterile filtering the supernatant obtained by said centrifuging and/or the filtrate obtained by said filtering by tangential flow filtration, preferably the filtrate obtained by said filtering by tangential flow filtration, through a sterile filter having a pore size of about 0.18 to 0.25 µm, preferably 0.20 to 0.22 µm, most preferably 0.22 µm.

The stability of many VLPs is established in a large extend by disulfide bounds between the capsid proteins forming said VLP. Generally, disulfide bounds are formed under oxidative and released under reductive conditions. It has been found that the stability of a VLP, preferably of a VLP comprising thiol groups capable of forming disulfide bounds such as, for example, VLP of bacteriophage Qβ, can be significantly increased by exposing said VLP to oxidative conditions prior to said purifying said VLP from said clarified homogenate. This can, for example, be achieved by agitating said clarified homogenate containing said VLP under condition allowing access of oxygen. In a further preferred embodiment said clarifying of said homogenate further comprises the step of exposing said VLP to oxidative conditions, wherein said exposing of said VLP to oxidative conditions is preferably performed after said centrifuging, after said filtering by tangential flow filtration or after said sterile filtering, wherein preferably said VLP is a VLP comprising thiol groups capable of forming disulfide bounds, more preferably a VLP of a RNA bacteriophage, still more preferably VLP of RNA bacteriophage AP205 or Qβ, most preferably VLP of RNA bacteriophage Qβ. In a preferred embodiment said exposing of said VLP to oxidative conditions is performed by slowly agitating said clarified homogenate under conditions allowing the access of oxygen, wherein preferably said agitating is performed at low temperature, preferably at 3 to 15° C., more preferably at 4 to 10° C., most preferably at 8° C. The time required for the complete formation of disulfide bounds mainly depends on the efficiency of oxygen introduction into said clarified homogenate and can be determined by analysing samples of said VLP by SDS PAGE under non-reducing conditions or by Ellman's test allowing the quantification of free thiol groups. Volumes of 500 ml up to 1000 l are preferably agitated for 1 h up to 16 h, most preferably for 8 to 10 h. The formation of disulfide bounds can further be improved by exposing said VLP to slightly alkaline conditions. In a preferred embodiment said exposing is performed in a buffer comprising a pH of 7.2 to 8.2, more preferably of 7.2 to 7.8, still more preferably 7.3 to 7.7, still more preferably 7.4 to 7.6, most preferably 7.5, wherein said pH refers to 20° C. In a further preferred embodiment said exposing of said VLP to oxidative conditions is performed in a buffer comprising 20 to 100 mM, preferably 30 to 70 mM, more preferably 40 to 60 mM, most preferably 50 mM Tris-HCl, and 1 to 25 mM, preferably 1 to 15 mM, more preferably 1 to 10 mM, most preferably 5 mM EDTA, wherein further preferably said buffer comprises an electric conductivity below 12 mS/cm, preferably below 10 mS/cm, most preferably below 8 mS/cm. In a very preferred embodiment said alkaline loading buffer comprises 50 mM Tric-HCl and 5 mM EDTA, wherein the pH at 22° C. is 7.4 (pH is 8.0 at 4° C.) and the electric conductivity is below 8 mS/cm. In a further preferred embodiment said exposing of said VLP to oxidative conditions is performed by contacting said VLP with oxidising compounds, wherein preferably said oxidising compounds are selected from the group consisting of: (a) oxidized glutathione (GSSG), (b) peroxides, preferably $H_2O_2$, and (c) metal ions, preferably $Cu^{++}$.

The chromatographies of the invention, preferably said first and said second chromatography, are typically and preferably performed in cylindrical columns packed with a chromatography matrix, preferably a hydroxyapatite matrix or an anion exchange matrix. Typically and preferably the chromatographies of the invention are performed using buffers referred to as equilibration buffer, washing buffer and elution buffer, wherein first equilibration buffer, first washing buffer and first elution buffer refer to the buffers used for said first chromatography and second equilibration buffer, second washing buffer and second elution buffer refer to the buffers used for said second chromatography. In a preferred embodiment, said chromatography matrix of said first chromatography and/or said hydroxyapatite matrix of said second chromatography, is equilibrated with said first/second equilibration buffer prior to said binding of said VLP to said chromatography matrix or said hydroxyapatite matrix. During said chromatographies said buffers are flowing through said chromatography matrix in a laminar flow, wherein preferably said flow is driven by gravitation, suction or pressure, preferably by pressure. However, any other technical setup known in the art and allowing to carry out chromatography may be equally useful.

The buffers used for the chromatographies of the invention, preferably said equilibration buffer, said washing buffer and said elution buffer of said first and/or second chromatography, typically and preferably comprise a pH which is about neutral, more preferably said pH is selected from 6.5, 6.6, 6.7, 6.8, 6.9, 7.0, 7.1, 7.2, 7.3, 7.4, 7.5, 7.6 and 7.8, still more preferably said pH is 7.0 to 7.4, still more preferably said pH is 7.1 to 7.3, most preferably said pH is 7.2. The pH of the buffers used for the chromatographies of the invention may be stabilized with any buffer system known in the art, preferably by a buffer system commonly used in biochemistry. Preferred buffer systems comprise a compound selected from the group consisting of: (a) HEPES (N-(2-Hydroxyethyl)piperazine-N'-(2-ethanesulfonic acid)), (b) MES (2-(N-Morpholino) ethanesulfonic acid), (c) MOPS (3-(N-Morpholino)propanesulfonic acid), (d) TAPS (N-tris[Hydroxymethyl]methyl-3-aminopropanesulfonic acid), (e) TRIS (tris(Hydroxymethyl) aminomethane, Tromethamine), (f) Bis-Tris(bis(2-Hydroxyethyl)amino-tris(hydroxymethyl)methane),(g) Bis-Tris Propane (1,3-bis(tris[Hydroxymethylmethylamino) propane), and (h) any combination and/or any derivative thereof. Any salt form of these compounds may be equally useful. Also inorganic buffer systems such as phosphate buffer or carbonate buffer may be useful for the invention. In a preferred embodiment the buffers used for the chromatographies of the invention, preferably said equilibration buffer, said washing buffer and said elution buffer of said first and/or second chromatography, comprise a phosphate buffer, preferably potassium or sodium phosphate buffer, most preferably sodium phosphate buffer. Phosphate buffer is a solution comprising a mixture of hydrogenphosphate and dihydrogenphosphate, wherein the pH of the solution is determined by the molar ratio of both components. The preparation of phosphate buffer is within the skill of the artisan. Furthermore, the artisan is aware that the presence of other salts may influence the pH of a phosphate buffer. In particular, the ratio of the salt components of a phosphate buffer needs to be adapted to the presence of potassium or sodium chloride to stabilise a certain pH. In a preferred embodiment the buffers used for the chromatographies of the invention, preferably said equilibration buffer, said washing buffer and said elution buffer of said first and/or second chromatography, comprise 1 to 100 mM, preferably 5 to 50 mM, more preferably 10 to 30 mM, still more preferably about 20 mM phosphate buffer, most preferably 20 mM phosphate buffer. In a very preferred embodiment said buffers comprise 20 mM sodium phosphate buffer.

Chromatography matrices useful in the process of the invention are materials capable of binding biochemical compounds, preferably proteins, nucleic acids, and/or endotoxins, wherein the affinity of said biochemical compounds to said chromatography matrix is influenced by the ion composition of the surrounding solution (buffer). Controlling the ion composition of said solution allows to use the chromatography materials of the invention either in subtractive mode (VLP passes through said chromatography matrix, at least certain contaminants bind to said chromatography matrix) or, preferably, in adsorptive mode (VLP binds to the chromatography matrix). Typically and preferably said VLP binds to said chromatography matrix, preferably to said first and/or to said second chromatography matrix, in the presence of at most about 400 mM, more preferably at most about 300 mM, most preferably 100 to 300 mM of said inorganic salt, wherein preferably said inorganic salt is potassium chloride or sodium chloride, most preferably sodium chloride. Preferred chromatography matrices of the invention are materials which are capable of reversibly binding said VLP. In one embodiment of the invention said first chromatography matrix and said second chromatography matrix, are selected from (a) anion exchange matrix, and (b) hydroxyapatite matrix.

In a preferred embodiment said first chromatography matrix and said second chromatography matrix, preferably said first chromatography matrix, is an anion exchange matrix, wherein preferably said anion exchange matrix comprises a functional anion exchange group, wherein further preferably said functional anion exchange group is a substituted amine, wherein still further preferably said substituted amine is selected from the group consisting of DEAE (diethylaminoethyl), DMAE (dimethylaminoethyl), TEAE (triethylaminoethyl), TMAE (trimethylaminoethyl), QAE (quaternary amino ethyl), QA (quaternary amine), and AE (aminoethyl). In very preferred embodiment said substituted amine is a quaternary amine group, wherein said quaternary amine group is selected from the group consisting of TEAE, TMAE, QAE, and QA. Most preferably said quaternary amine group is TMAE (trimethylaminoethyl).

In a preferred embodiment said first chromatography matrix and said second chromatography matrix, preferably said first chromatography matrix, is an anion exchange matrix, preferably selected from the group consisting of: (a) Matrex® Silica PEI high performance anion exchanger, (b) POROS® HQ, (c) a monolithic anion exchange matrix, preferably a convective interaction medium (e.g. CIM®-QA (quarternary amino group, BIA Separations Cat. No. 210.5113) or CIM-DEAE (diethylamine, BIA Separations Cat. No. 210.5114), and, very preferably, (d) a tentacle anion exchange matrix.

In a preferred embodiment said first chromatography matrix and said second chromatography matrix, preferably said first chromatography matrix, is a tentacle anion exchange matrix, preferably comprising resin particles comprising, preferably on their surface, spacers formed by linear polymer chains (tentacles), wherein said tentacles are substituted with functional groups having anion exchange activity. In a preferred embodiment said resin particles are particles of methacrylate or polyvinylstyrene polymers, preferably comprising a pore size of about 800 Å, wherein still more preferably said methacrylate or polyvinylstyrene polymer are crosslinked. Most preferably said resin particles consist of crosslinked methacrylate polymer. In a further preferred embodiment said functional group is selected from the group consisting of TMAE (Trimethylaminoethyl-), DMAE (Dimethylaminoethyl-), and DEAE (Diethylaminoethyl-). In a very preferred embodiment said functional group is DEAE or TMAE, most preferably TMAE. In a further preferred embodiment said polymer chains forming said tentacles are acrylamide polymers. In a very preferred embodiment said tentacle anion exchange matrix comprises (i) resin particles of methacrylate polymer or of vinyl polymer, preferably of methacrylate polymer, most preferably of cross-linked methacrylate polymer, (ii) acrylamide tentacles, wherein preferably said acrylamide tentacles attached to the surface of said resin particles, and wherein said acrylamide tentacles are substituted with TMAE (Trimethylaminoethyl-) groups.

Specifically preferred tentacle ion exchange matrices are Fractogel® EMD TMAE ion exchangers and Fractoprep® DEAE ion exchangers (Merck), most preferred tentacle ion exchange matrices are Fractogel® ion EMD TMAE exchangers.

Hydroxyapatite matrices are capable of reversibly binding said VLP not only via their anion exchange activity but also via additional mechanisms, including for example dipol-dipol interactions, and thus allow very efficient reversible binding of said VLP. Therefore, in a further preferred embodiment said first chromatography matrix and said second chromatography matrix, preferably said second chromatography matrix, is a hydroxyapatite matrix, preferably Macro-Prep® ceramic Hydroxyapatite.

In a very preferred embodiment said first chromatography matrix is a hydroxyapatite matrix or an anion exchange matrix, preferably a hydroxyapatite matrix or a tentacle anion exchange matrix, more preferably a tentacle anion exchange matrix, still more preferably a Fractogel® EMD TMAE ion exchanger or a Fractoprep® DEAE ion exchanger, most preferably a Fractogel® ion EMD TMAE exchanger; and said second chromatography matrix is a hydroxyapatite matrix, preferably Macro-Prep® ceramic Hydroxyapatite.

Fractogel® ion exchangers are cross-linked porous polymethacrylate resins with pore-sizes of about 800 Å modified according to the tentacle technology in which functionally substituted acrylamides are grafted to the surface of the particles. This linking of the functional ion exchanger groups via linear polymer chains renders the ionic groups more readily accessible for proteins.

Fractoprep® ion exchangers are produced employing the same principle as for Fractogel® ion exchangers but with a vinyl polymer resin base particle.

Macro-Prep® ceramic hydroxyapatite media are a spherical, macroporous form of hydroxyapatite. They are produced by sintering crystalline Hydroxyapatite at high temperatures. Type I and II differ in the sintering temperature used for their production which results in a different surface composition and different pore sizes of the particles (600-800 Å for Type I, 800-1000 Å, for Type II).

Matrex Silica® PEI high performance anion exchange stationary phases are based on wide pore silica (available with 500 Å and 1,000 Å pore diameter).

POROS® HQ is based on a quaternized polyethyleneimine functional group yielding a high capacity, Perfusion Chromatography® media designed for the separation and purification of biomolecules.

The main portion of host cell derived impurities remaining in the clarified homogenate of the bacterial host is removed by said purifying said VLP from the clarified homogenate obtained by said clarifying in a first chromatography, said chromatography comprising the steps of: (i) binding said VLP to a first chromatography matrix, wherein preferably said first chromatography matrix is a hydroxyapatite matrix or an anion exchange matrix, more preferably a hydroxyapatite matrix or a tentacle anion exchange matrix, most preferably a tentacle anion exchange matrix, (ii) washing said first chromatography matrix, and (iii) eluting said VLP from said first chromatography matrix.

In one embodiment said first chromatography matrix is selected from the group consisting of: (a) Fractogel® EMD TMAE (M), preferably having a particle size of 40-90 μm; (b) Fractogel® EMD TMAE Hicap (M), preferably having a particle size of 40-90 μm; (c) Fractoprep® DEAE, preferably having a particle size of 30-150 μm; (d) Macro-Prep® CHT Ceramic Hydroxyapatite Type I, preferably having a particle size of about 80 μm; (e) Macro-Prep® CHT Ceramic Hydroxyapatite Type II, preferably having a particle size of about 80 μm; (f) Matrex® Granular Silica PEI-300 Å, preferably having a particle size of 35-70 μm; (g) Matrex® Granular Silica PEI-1000 Å, preferably having a particle size of 35-70 μm; (h) Poros 50 HQ, (i) CIM®-QA (quarternary amino group, BIA Separations Cat. No. 210.5113), and (j) CIM®-DEAE.

In one embodiment said first chromatography further comprises the step of equilibrating said first chromatography matrix with a first equilibration buffer, wherein said equilibrating is performed prior to said binding of said VLP. In a preferred embodiment said first equilibration buffer comprises an inorganic salt, preferably an alkaline metal halogenide, more preferably potassium chloride or sodium chloride, most preferably sodium chloride, wherein preferably the concentration of said inorganic salt is chosen to facilitate reversible binding of said VLP to said first chromatography matrix. In a further preferred embodiment said inorganic salt is an ammonium salt, preferably ammonium sulphate or ammonium acetate. It is apparent for the artisan that a salt concentrations above a certain threshold will lead to incomplete binding of the VLP and, consequently, to loss of VLP. In a very preferred embodiment said first equilibration buffer comprises 50 to 200 mM, preferably 100 to 180 mM, more preferably about 150 mM of potassium chloride or sodium chloride, preferably sodium chloride. In a further preferred embodiment, said first equilibration buffer comprises at most about 200, more preferably at most about 150 mM sodium chloride. In a further preferred embodiment said first equilibration buffer comprises a pH which is about neutral, preferably said pH is 7.2. In a very preferred embodiment said first chromatography matrix is Fractogel® EMD TMAE and said first equilibration buffer is PBS buffer (Example 4).

In one embodiment said binding of said VLP to said first chromatography matrix is performed by passing said clarified homogenate containing said VLP through said first chromatography matrix and, optionally, removing unbound material by further passing equilibration buffer through said chromatography matrix, wherein preferably the volume of said equilibration buffer is 1 to 5 times, more preferably 2 to 4 times, most preferably 3 times the volume of said first chromatography matrix. Alternatively, said removing of unbound material is performed by further passing a buffer through said chromatography matrix, wherein said buffer has the same composition as the buffer used for said exposing said VLP to oxidative conditions, and wherein preferably the volume of said buffer is 1 to 5 times, more preferably 2 to 4 times, most preferably 3 times the volume of said first chromatography matrix.

In one embodiment said first chromatography comprises the step of washing said first chromatography matrix, wherein said washing is performed with said first washing buffer. In a preferred embodiment said first washing buffer comprises an inorganic salt, preferably a halogenide of an alkaline metal, more preferably sodium chloride or potassium chloride, most preferably sodium chloride. In a preferred embodiment said first washing buffer comprises the same inorganic salt as said first equilibration buffer, wherein preferably said inorganic salt is sodium chloride or potassium chloride, most preferably sodium chloride. The purity of the eluted VLP will depend on the salt concentration of said first washing buffer. Washing buffer comprising a higher salt concentration will remove contaminating compounds more efficiently than a washing buffer comprising a lower salt concentration, whereas a washing buffer comprising a salt concentration above a certain threshold may cause loss of bound VLP.

In a preferred embodiment said washing of said first chromatography matrix, is performed with a first washing buffer comprising 300 to 500 mM, 350 to 480 mM, 380 to 450 mM, 400 to 440 mM, or 410 to 430 mM of an inorganic salt, preferably of sodium chloride or potassium chloride, most preferably of sodium chloride. In a very preferred embodiment said first washing buffer comprises about 425 mM of said inorganic salt, preferably sodium chloride or potassium chloride, most preferably sodium chloride, wherein further preferably said first chromatography matrix is an anion exchange matrix, more preferably a tentacle anion exchange matrix, most preferably Fractogel EMD TMAE. In a still more preferred embodiment said first washing buffer is PBS425 (Example 4). Typically and preferably, said washing of said first chromatography matrix is performed with a volume of said first washing buffer which equals 1 to 10 times, preferably 3 to 8 times most preferably about 5 times the volume of said first chromatography matrix. Alternatively, said washing of said first chromatography matrix is continued until the concentration of protein as detected by UV absorption at 280 and 300 nm of said washing buffer after passing through said chromatography matrix is below a desired threshold.

In one embodiment said first chromatography comprises the step of eluting said VLP from said first chromatography matrix, wherein said eluting is performed with a first elution buffer comprising an inorganic salt, preferably an alkaline metal halogenide, more preferably potassium chloride or sodium chloride, most preferably sodium chloride. In a preferred embodiment said first elution buffer comprises the same inorganic salt as said first equilibration buffer and/or said first washing buffer. The purity of the eluted VLP will depend on the salt concentration of the elution buffer. Elution buffer comprising higher salt concentrations may elute more contaminating compounds than those comprising lower salt concentrations, whereas elution buffers comprising salt at a concentration below a certain threshold may cause loss VLP due to insufficient elution and result in large elution volumes. For the purpose of efficient up-scaling of the process, efficient elution of the VLP in minimal elution volumes is desired. Therefore, in a preferred embodiment said eluting of said VLP from said first chromatography matrix is performed with a first elution buffer comprising a concentration of said inorganic salt of at least about 480, 490, 400, 510, 520, 530, 540, 550, 560, 570, 580, 590 or 600 mM, wherein said inorganic salt is preferably a halogenide of an alkaline metal, more preferably sodium chloride or potassium chloride, most preferably sodium chloride. In a very preferred embodiment said eluting is performed with a first elution buffer comprising 500 to 600 mM, preferably 520 to 580 mM, more preferably 530 to 570 mM, still more preferably 540 to 560 mM, most preferably about 550 mM of said inorganic salt, preferably of sodium chloride or potassium chloride, most preferably of sodium chloride. In a very preferred embodiment said first elution buffer is PBS550 (Example 4). In another embodiment eluting of said VLP from said first chromatography matrix is performed with a concentration gradient of said inorganic salt. Depending on the specific biochemical features of the VLP and of said first chromatography matrix the separation of the VLP from contaminating compounds may be improved by application of linear or non-linear concentration gradients. In a preferred embodiment said eluting of said VLP, preferably of a VLP of RNA bacteriophage Qβ, from said first chromatography matrix is performed with a linear gradient of said inorganic salt in said first elution buffer, wherein said linear gradient preferably ranges from 300 to 900 mM, more preferably from 400 to 700 mM, most preferably from 425 to 650 mM; and wherein further preferably the volume of said first elution buffer is 1 to 5 times, preferably 2 to 4 times, most preferably 3 times the volume of said chromatography matrix; and wherein still further preferably said inorganic salt is sodium chloride or potassium chloride, most preferably sodium chloride; and wherein still further preferably said first chromatography matrix is an anion exchange matrix, more preferably a tentacle anion exchange matrix, most preferably Fractogel EMD TMAE.

In a further preferred embodiment said first chromatography matrix is a hydroxyapatite matrix, preferably hydroxyapatite matrix comprising a pore size of 800-1000 Å, and said eluting is performed using a co-gradient of a hydrogenphosphate/dihydrogenphosphate and an inorganic salt, wherein said inorganic salt preferably is a halogenide of an alkaline metal, more preferably a chloride, still more preferably potassium chloride or sodium chloride, most preferably sodium chloride. In a very preferred embodiment said eluting is performed by a co-gradient of sodium hydrogenphosphate/dihydrogenphosphate and sodium chloride.

The elution profile of the VLP from the anion exchange matrix can be monitored by registration of the UV absorption, wherein registration of the UV absorption at 280 and 300 nm is especially useful for the detection of VLPs of RNA bacteriophages, preferably of VLPs of RNA bacteriophage Qβ. The artisan is able to interpret such elution profiles and to identify the fractions containing the purified VLP. For example, in case said first chromatography matrix is an anion exchange matrix and said first elution buffer comprises 550 mM sodium chloride, the VLP is typically contained in the fraction from about 0.5 to about 2 times the volume of the anion exchange matrix. In case said first chromatography matrix is an anion exchange matrix and said first elution buffer comprises a gradient of 425 to 650 mM sodium chloride in three times the volume of said anion exchange matrix, the VLP is typically contained in the fraction from about 1.3 to about 2.6 times the volume of the anion exchange matrix. In one embodiment said purifying of said VLP from said clarified homogenate further comprises the step of obtaining the fraction of the eluate of said first chromatography containing said VLP. In a further embodiment said purifying of said VLP from said clarified homogenate further comprises the step of diluting said fraction in such a way that the concentration of said inorganic salt in said fraction is in a range which allows binding of said VLP to said second chromatography matrix. Typically and preferably, said fraction is diluted in a ratio of about 1:2 with a buffer which is essentially free of said inorganic salt. In a preferred embodiment, said fraction is diluted in such a way that the concentration of said inorganic salt is 100 to 400 mM, preferably 200 to 400 mM, more preferably 200 to 300 mM, most preferably about 250 mM. In a further embodiment said purifying of said VLP from said clarified homogenate further comprises the optional step of sterile filtering the eluate of said first chromatography, said fraction containing said VLP, or said diluted fraction through a sterile filter having a pore size of about 0.18 to 0.25 μm, preferably 0.20 to 0.22 μm, most preferably 0.22 μm.

The process of the invention further comprises a second chromatography, wherein said second chromatography is particularly efficient in removing endotoxin contaminations. In one embodiment said further purifying said VLP in a second chromatography from the eluate obtained by said first chromatography; or, preferably, from said fraction containing said VLP or from the filtrate obtained by said optional sterile filtering; said second chromatography comprising the steps of: (i) binding said VLP to a second chromatography matrix, wherein preferably said second chromatography matrix is a hydroxyapatite matrix; (ii) washing said second chromatography matrix; and (iii) eluting said VLP from said second chromatography matrix.

In a preferred embodiment said second chromatography matrix is a hydroxyapatite matrix, wherein preferably said hydroxyapatite matrix is a ceramic hydroxyapatite matrix, wherein preferably said ceramic hydroxyapatite matrix comprises a particle size of about 80 μm and a pore size of the particles of about 800-1000 Å. In a very preferred embodiment said hydroxyapatite matrix is a Macro-Prep® CHT Ceramic Hydroxyapatite matrix. In a still more preferred embodiment said hydroxyapatite matrix is Macro-Prep® CHT Ceramic Hydroxyapatite Type II.

In a further preferred embodiment said second chromatography comprises the step of equilibrating said second chromatography matrix with a second equilibration buffer, wherein said second equilibration buffer preferably comprises an inorganic salt, wherein further preferably said second equilibration buffer comprises said inorganic salt in a concentration which facilitates binding of said VLP to said second chromatography matrix, wherein further preferably said second chromatography matrix is a hydroxyapatite matrix. In a preferred embodiment said concentration of said inorganic salt in said second equilibration buffer is at most 400 mM, preferably at most 300 mM.

It was found that binding of the VLP to a hydroxyapatite matrix in the absence of an inorganic salt is instable and causes loss of VLP during the following washing step, while salt concentrations above a certain threshold will lead to incomplete binding. In a preferred embodiment said second equilibration buffer comprises the same inorganic salt as said first equilibration buffer and/or said first washing buffer and/or said first elution buffer. In a further preferred embodiment said second chromatography matrix is a hydroxyapatite matrix and said second equilibration buffer comprises 50 to 200 mM, preferably 100 to 180 mM, more preferably about 150 mM of potassium chloride or sodium chloride, preferably sodium chloride. In a very preferred embodiment said second equilibration buffer is PBS (Example 5).

In a preferred embodiment said binding of said VLP to said second chromatography matrix, preferably to said hydroxyapatite matrix, is performed in the presence of 100 to 400 mM, preferably 200 to 400 mM, more preferably 200 to 300 mM, most preferably about 250 mM of said inorganic salt, wherein said inorganic salt preferably is potassium chloride or sodium chloride, most preferably sodium chloride.

In a further embodiment said washing of said second chromatography matrix is performed with a second washing buffer, wherein preferably said second washing buffer comprises an inorganic salt, preferably a halogenide of an alkaline metal, more preferably sodium chloride or potassium chloride, most preferably sodium chloride. In a preferred embodiment said second washing buffer comprises the same inorganic salt as said second equilibration buffer, preferably sodium chloride or potassium chloride, most preferably sodium chloride. The purity of the eluted VLP will depend on the salt concentration of the second washing buffer. Washing buffers comprising higher salt concentrations will remove contaminating compounds more efficiently than those comprising lower salt concentrations, whereas washing buffers comprising salt at a concentration beyond a certain threshold may cause loss of bound VLP. In a preferred embodiment said second washing buffer comprises 50 to 400 mM, preferably 100 to 300 mM, more preferably 120 to 200 mM, still more preferably 130 to 170 mM, still more preferably 140 to 160 mM, most preferably 145 to 155 mM of said inorganic salt, preferably of sodium chloride or potassium chloride, most preferably sodium chloride. In a very preferred embodiment said second washing buffer comprises 150 mM of said inorganic salt, preferably of sodium chloride or potassium chloride, most preferably sodium chloride. In a still more preferred embodiment said second washing buffer is PBS (Example 5). In a further preferred embodiment said washing of said second chromatography matrix, is performed by passing said second washing buffer through said second chromatography matrix, wherein the volume of said second washing buffer passed through said second chromatography matrix preferably is 1 to 10 times, more preferably 3 to 8 times, most preferably 5 times the volume of said second chromatography matrix.

In a further embodiment said second chromatography comprises the step of eluting said VLP from said second chromatography matrix, wherein said eluting is performed by a second elution buffer, wherein said second elution buffer preferably comprises an inorganic salt, wherein further preferably said inorganic salt is an alkaline metal halogenide, more preferably potassium chloride or sodium chloride, most preferably sodium chloride. In a further preferred embodiment said second elution buffer comprises an inorganic salt, wherein preferably said inorganic salt is the same salt as contained in said second equilibration buffer and/or said second washing buffer. In a further embodiment said eluting of said VLP from said second chromatography matrix is performed with an elution buffer comprising a concentration of said inorganic salt of at least about 900, 1000, 1200, 1500, 2000 or 3000 mM, wherein said inorganic salt is preferably a halogenide of an alkaline metal, more preferably sodium chloride or potassium chloride, most preferably sodium chloride.

In a further preferred embodiment said second elution buffer comprises a combination of phosphorous salts (phosphate buffer), preferably hydrogenphosphate and dihydrogenphosphate of potassium or sodium, preferably of sodium. In a preferred embodiment said second elution buffer comprises 200 to 500 mM, more preferably 200 to 400 mM, most preferably about 300 mM phosphate buffer, preferably sodium phosphate buffer.

A second elution buffer only containing said alkaline metal halogenide either requires a high concentration of said alkaline metal halogenide which may lead to the precipitation of said VLP or, at lower salt concentrations, leads to high elution volumes which are undesired with respect to the up-scale of the process. A second elution buffer which is essentially free of said alkaline metal halogenide and only based on said combination of phosphorous salts would, on the other hand, also result in high eluate volumes. It was found that second elution buffers comprising a combination of both, said alkaline metal halogenide and said combination of phosphorous salts (phosphate buffer), allow for efficient elution of said VLP, for minimizing the elution volume, for minimizing the total salt concentration in the eluate, and, thus, for efficient up-scaling of the process. In a further preferred embodiment said second elution buffer therefore comprises a mixture of said alkaline halogenide and of said combination of phosphorous salts, wherein preferably the concentration of said combination of phosphorous salts is the lowest concentration allowing elution of said VLP when said combination of phosphorous salts is used alone, i.e. in the absence of said alkaline metal halogenide. In a very preferred embodiment said second elution buffer comprises an alkaline metal halogenide, preferably potassium chloride or sodium chloride, most preferably sodium chloride; and a combination of phosphorous salts, preferably potassium or sodium hydrogenphosphate/dihydrogenphosphate, most preferably sodium hydrogenphosphate/dihydrogenphosphate, wherein preferably the concentration of said alkaline metal halogenide is 900 to 1200 mM, more preferably about 900 mM; and wherein further preferably the concentration of said combination of phosphorous salts is 200 to 300 mM, most preferably about 200 mM; and wherein still further preferably said VLP is a VLP of RNA bacteriophage Qβ. In a very preferred embodiment said second elution buffer is HSB and said VLP preferably is a VLP of RNA bacteriophage Qβ (Example 5).

In a further preferred embodiment said second elution buffer comprises an alkaline metal halogenide, preferably potassium chloride or sodium chloride, most preferably sodium chloride; and a combination of phosphorous salts, preferably potassium or sodium hydrogenphosphate/dihydrogenphosphate, most preferably sodium hydrogenphosphate/dihydrogenphosphate, wherein preferably the concentration of said alkaline metal halogenide is 50 to 500 mM, more preferably about 250 mM; and wherein further preferably the concentration of said combination of phosphorous salts is 10 to 200 mM, most preferably about 50 mM; and wherein still further preferably said VLP is a VLP of RNA bacteriophage AP205.

In a further preferred embodiment said eluting of said VLP from said second chromatography matrix is performed with a concentration gradient of said inorganic salt in said second elution buffer. Depending on the specific features of the VLP and the hydroxyapatite matrix the separation of the VLP from contaminating compounds may be improved by application of linear or non-linear concentration gradients. For example, the VLP may be eluted with a concentration gradient of said alkaline metal halogenide from 900 to 3000 mM and/or a concentration gradient of said phosphorous salt from 100 to 400 mM.

The elution profile of said VLP from said second chromatography matrix can be monitored by registration of the UV absorption, wherein registration of the UV absorption at 280 and 300 nm is especially useful for the detection of VLPs of RNA bacteriophages, preferably of VLPs of RNA bacteriophage Qβ. The artisan is able to interpret such elution profiles and to identify the fractions containing the purified VLP. As an example, in case said second chromatography matrix is hydroxyapatite and said second elution buffer comprises 900 mM sodium chloride and 200 mM sodium hydrogenphosphate/dihydrogenphosaphate, said VLP is typically contained in the fraction from about 0.5 to about 3 times the volume of said second chromatography matrix.

The purity of the VLP preparation may be assessed by analytical size exclusion chromatography (Example 7). Remaining contamination of the VLP preparation with host cell protein may also be detected by immunological means, for example by a ELISA detecting *E. coli* derived protein (e.g. *E. coli* HCP ELISA kit, Cygnus Technologies Inc., cat. nos. F010 and F410). The VLP contained in the eluate of said second chromatography may be desalted and, if required, finally purified in a so called "polishing step". In a further preferred embodiment the process of the invention comprises the step of finally purifying said VLP, wherein preferably said finally purifying of said VLP is performed by precipitating said VLP, preferably with ammonium sulphate, and preferably by at least one subsequent third chromatography, wherein preferably said at least one subsequent third chromatography is a size exclusion chromatography. In a more preferred embodiment said finally purifying said VLP is performed by at least one third chromatography, wherein preferably said at least one third chromatography is selected from the group consisting of: (a) immobilised metal ions affinity chromatography (IMAC), preferably IMC in subtractive mode (contaminants selectively bind to the chromatography matrix); (b) hydrophobic interaction chromatography (HIC), wherein said HIC may be performed in subtractive or in adsorptive mode; (c) membrane adsorption and (d) size exclusion chromatography. In a further preferred embodiment said at least one third chromatography comprises membrane adsorption, wherein preferably said membrane adsorption is performed with an adsorption membrane selected from the group consisting of: (a) polyethylenimine coated membrane, preferably PALL, Mustang E, Cat. No. CLM05MSTGEP1, CL3MSTGEP1, NP6MSTGEP1, NP7MSTGEP1, or NP8MSTGEP1; and (b) adsorber membranes comprising quarternary amino groups, preferably Pall Mustang Q, Pall, Cat. No. CLM05MSTGQP1 or Sartorius Sartobind Q-membrane adsorber (Sartorius, Cat. No. Q15X; Q100X). In a further preferred embodiment said at least one third chromatography comprises a hydrophobic interaction chromatography (HIC, Example 14) followed by a size exclusion chromatography. In a further preferred embodiment said at least one third chromatography comprises a immobilised metal ions affinity chromatography (IMAC, Example 15), wherein preferably said metal ions are $Zn^{++}$ ions or $Cu^{++}$ ions, and wherein further preferably said IMAC is performed in subtractive mode (contaminants bind to chromatography matrix); wherein further preferably said IMAC is followed by size exclusion chromatography.

Size exclusion chromatography is useful for further purifying and/or re-buffering said VLP. In a very preferred embodiment said at least one third chromatography is at least one, preferably exactly one, size exclusion chromatography. In a preferred embodiment said size exclusion chromatography comprises the steps of loading said fraction of the eluate of said second chromatography to a gel filtration matrix, wherein said gel filtration matrix preferably is equilibrated with a buffer having a composition which is desired for storage or further processing of said VLP. In a preferred embodiment said buffer comprises an inorganic salt, preferably a halogenide of an alkaline metal, more preferably potassium chloride or sodium chloride, most preferably sodium chloride, wherein the concentration of said inorganic salt is about 50 to 500 mM, preferably 100 to 300, most preferably about 150 mM.

In case no remaining contaminants are detectable in the preparation of said VLP, e.g. the elution profile of said analytical size exclusion chromatography does not reveal extra peaks, said gel filtration matrix preferably is a desalting matrix. In a preferred embodiment said gel filtration matrix is a desalting matrix, wherein said desalting matrix preferably is a Sephadex matrix, most preferably Sephadex G-25.

In case the VLP preparation still comprises contaminants as, for example detected by analytical size exclusion chromatography, ELISA (e.g. *E. coli* HCP ELISA kit, Cygnus Technologies Inc., cat. nos. F010 and F410) or any other assay, said gel filtration matrix preferably is a matrix having a separation characteristic within the range of $2 \times 10^4$ to $2 \times 10^7$ Dalton. In a preferred embodiment said gel filtration matrix is a gel filtration matrix having a separation characteristic within the range of $2 \times 10^4$ to $2 \times 10^7$ Dalton. In a further preferred embodiment said gel filtration matrix is selected from the group consisting of: (a) Sepharose 4 FF, (b) Sephacryl-S500 HR, (c) Sephacryl-S1000 SF, (d) Toyopearl HW-65F, (e) Sepharose CL-4B and (f) Sephacryl-S400. Most preferably, said gel filtration matrix is Sepharose CL-4B. Said size exclusion chromatography further comprises the step of eluting the VLP from said gel filtration matrix by isocratic elution, i.e. the elution buffer has about the same, preferably the same composition as the buffer used for equilibration. The UV absorption of the flow through is recorded, preferably at 280 nm and 300 nm, the fraction containing the VLP is collected.

In a further embodiment the process further comprises the step of sterile filtering said VLP, wherein the fraction containing the VLP of the eluate of said at least one third chromatography, preferably of said size exclusion chromatography, is filtrated through a sterile filter, preferably having a pore size of about 0.18 to 0.25 μm, preferably 0.20 to 0.22 μm, most preferably 0.22 μm.

In a further embodiment said finally purifying said VLP by said at least one third chromatography comprises the step of concentrating the solution comprising said VLP by filtration, preferably by tangential flow filtration, most preferably by tangential flow filtration using a Biomax 100 membrane, wherein preferably said concentrating is performed prior to the last of said at least one third chromatography, wherein further preferably the last of said at least one third chromatography is a size exclusion chromatography.

The purified VLP may by stored at $-75 \pm 15°$ C. until further processing.

As the process of the invention is a process for the purification of self-assembled VLP, it is neither possible nor intended to remove host cell derived nucleic acids and host cell derived proteins which are encapsulated inside the VLP using the process of the invention. Encapsulated host cell derived nucleic acids and host cell derived proteins often are an essential stabilizing element of the VLP and constitute an integral element of the VLP. They are therefore not regarded as impurities in the context of this invention. Recombinantly expressed self-assembled VLPs contain host cell derived nucleic acids and host cell derived protein in a rather constant ratio relative to the amount of capsid protein forming the VLP, wherein this ratio may differ between different VLP species. As an example, purified recombinantly expressed and self-assembled VLP of RNA bacteriophage Qβ typically contains per 100 μg Qβ capsid protein about 25 to 35 μg RNA, about 4 to 6 ng host cell DNA and about 2 μg host cell protein.

A very preferred embodiment of the invention is a process for the purification of a VLP of bacteriophage Qβ from a recombinant bacterial host expressing said VLP, the process comprising the steps of: (a) homogenizing said bacterial host; (b) clarifying the homogenate obtained by said homogenizing; (c) purifying said VLP from the clarified homogenate obtained by said clarifying in a first chromatography comprising the steps of: (i) binding said VLP to a Fractogel® EMD TMAE (M) matrix in the presence of at most 150 mM sodium chloride; (ii) washing said Fractogel® EMD TMAE (M) matrix in the presence of about 425 mM sodium chloride; and (iii) eluting said VLP from said Fractogel® EMD TMAE (M) matrix in the presence of about 550 mM sodium chloride; wherein said first chromatography is performed at a pH of 7.2; (d) further purifying said VLP from the eluate obtained by said first chromatography in a second chromatography comprising the steps of: (i) binding said VLP to a Macro-Prep® CHT Ceramic Hydroxyapatite Type II matrix in the presence of about 250 mM sodium chloride; (ii) washing said Macro-Prep® CHT Ceramic Hydroxyapatite Type II matrix in the presence of about 150 mM sodium chloride; (iii) eluting said VLP from said Macro-Prep® CHT Ceramic Hydroxyapatite Type II matrix in the presence of about 900 mM sodium chloride and about 200 mM sodium phosphate buffer; wherein said second chromatography is performed at a pH of about 7.2; and (e) finally purifying said VLP contained in the eluate of said second chromatography by at least one third chromatography, wherein said at least one third chromatography is exactly one size exclusion chromatography, wherein said size exclusion chromatography is performed in the presence of about 150 mM sodium chloride, and wherein further said size exclusion chromatography is performed using a gel filtration matrix, wherein said gel filtration matrix is Sepharose CL-4B; wherein said steps are performed in the given order.

A further preferred embodiment of the invention is a process for the purification of a VLP of bacteriophage AP205 from a recombinant bacterial host expressing said VLP, the process comprising the steps of (a) homogenizing said bacterial host; (b) clarifying the homogenate obtained by said homogenizing; (c) purifying said VLP from the clarified homogenate obtained by said clarifying in a first chromatography comprising the steps of: (i) binding said VLP to a Fractogel® EMD TMAE (M) matrix in the presence of at most 150 mM sodium chloride; (ii) washing said Fractogel® EMD TMAE (M) matrix in the presence of about 425 mM sodium chloride; and (iii) eluting said VLP from said Fractogel® EMD TMAE (M) matrix in the presence of about 550 mM sodium chloride; wherein said first chromatography is performed at a pH of 7.2; (d) further purifying said VLP from the eluate obtained by said first chromatography in a second chromatography comprising the steps of: (i) binding said VLP to a Macro-Prep® CHT Ceramic Hydroxyapatite Type II matrix in the presence of about 100 mM sodium chloride and at most about 5 mM sodium phosphate buffer; (ii) washing said Macro-Prep® CHT Ceramic Hydroxyapatite Type II matrix in the presence of about 100 mM sodium chloride and at most about 5 mM sodium phosphate buffer; (iii) eluting said VLP from said Macro-Prep® CHT Ceramic Hydroxyapatite Type II matrix in the presence of about 250 mM sodium chloride and about 50 mM sodium phosphate buffer; wherein said second chromatography is performed at a pH of about 7.2; and (e) finally purifying said VLP contained in the eluate of said second chromatography by at least one third chromatography, wherein said at least one third chromatography is exactly one size exclusion chromatography, wherein said size exclusion chromatography is performed in the presence of about 150 mM sodium chloride, and wherein further said size exclusion chromatography is performed using a gel filtration matrix, wherein said gel filtration matrix is Sepharose CL-4B; wherein said steps are performed in the given order.

EXAMPLES

Example 1

Cell Disruption

Solutions used for this process step were composed as described in Table 1.

TABLE 1

Composition of process solutions for cell disruption.

| EB⁻-buffer | 43.89 mM | Tris•HCl |
| | 6.11 mM | Tris Base |
| | 5.0 mM | EDTA Na3•3H2O |
| 10% Triton ® X-100 | 10% (v/v) | Triton ® X-100 |
| saturated Tris Base | 500 g/l | Tris Base |

Cell disruption of *E. coli* cells expressing Qβ was performed as follows: Bacterial cell pellets retrieved from the −80° C. storage device were thawed by resuspension in 2 ml EB⁻-buffer per 1 g cell pellet at 24° C. The thawed suspension was degassed for 10-15 minutes under vacuum before 10% Triton® X-100 was added to a final concentration of 0.1% (v/v). After stirring for 5 minutes, the cells were disrupted by three passages at 700±50 bar through an APV LAB 1000 high pressure liquid homogenizer (HPLH). The resulting homogenate was adjusted to pH≧7.8 by the addition of saturated Tris base and diluted 1:2 with EB⁻-buffer.

Example 2

Tangential Flow Filtration (TFF) and Sterile Filtration

A new TFF membrane suitable for the processing of high viscosity media, e.g. PVDF (Pellicon, Millipore), stabilized cellulose (Sartocon, Sartorius) and Polyethersulfon (SUPOR Pall), equipped with a 0.45 μm pore width membrane and an effective membrane area of 0.1 m² for homogenate derived from 400 g cell wet weight was sanitized and equilibrated with EB⁻-buffer. The feed and retentate outlets of the membrane holder were connected to a container containing diluted homogenate derived from 400 g cell wet weight. Diafiltration against EB⁻-buffer with a feed pressure of 1.0±0.2 bar was performed until two times the volume of the diluted homogenate had been collected as permeate. The permeate was filtrated over a 0.22 μm pore width sterilizing grade filtering unit and stored at 4° C.

Example 3

Clarification by Centrifugation as Alternative to Tangential Flow Filtration

The homogenate produced in Example 2 was not diluted prior to this step. The homogenate was centrifuged at 4° C. for 105 minutes at 10.000 g. The supernatant was decanted from the pellet without transferring the soft overlay and recentrifuged at 4° C. for 60 minutes at 10.000 g. The supernatant was decanted from any pellet present, diluted 1:2 with EB⁻-buffer, filtrated over a 0.22 μm pore width sterilizing grade filtering unit and stored at 4° C.

Example 3a

Clarification by a Combination of Centrifugation and TFF

The homogenate produced in Example 2 was not diluted prior to this step. The homogenate was centrifuged at 4° C. for 120 minutes at 10.000 g. The supernatant was decanted from the pellet without transferring the soft overlay and subjected to tangential flow filtration as described in Example 2.

Example 4

Anion Exchange (AIX) Chromatography on Fractogel EMD TMAE

TABLE 2

Composition of process solutions for AIX chromatography

| | Buffers | | |
|---|---|---|---|
| Component | PBS | PBS425 | PBS550 |
| $Na_2HPO_4 \cdot 2H_2O$ | 15.15 mM | 16.47 mM | 16.98 mM |
| $NaH_2PO_4 \cdot 2H_2O$ | 4.85 mM | 3.53 mM | 3.02 mM |
| NaCl | 150 mM | 425 mM | 550 mM |

The AIX chromatography was performed as follows: Sterile filtrated cleared cell homogenate produced either by TFF (Example 2) or by centrifugation (Example 3) was loaded on a Fractogel EMD TMAE column (bed volume of 350-450 ml for a sample derived from 80 g cell wet weight) equilibrated in PBS buffer. Unbound proteins were washed of the column with about 3 column volumes PBS and weakly bound impurities were eluted with 5 column volumes PBS425 before Qβ VLP was eluted with PBS550. Qβ VLP of sufficient purity for further processing eluted between 0.3 and 0.8 column volumes after the step to PBS550. Alternatively, Qβ VLP was eluted with PBS comprising a gradient of NaCl from 425 mM to 650 mM in 3 column volumes.

Example 5

Chromatography on Ceramic Hydroxyapatite (cHA)

The cHA chromatography was performed as follows: Peak fractions from the separation on Fractogel EMD TMAE were pooled and diluted 1:2 with NaPP-buffer pH 7.0. The diluted sample was filtrated using a 0.22 μm pore width sterilizing grade filter unit and loaded on a Macro-Prep ceramic Hydroxyapatite Type II column (bed volume of 125-175 ml for sample derived from 80 g cell wet weight) equilibrated in PBS. Unbound sample was eluted with 5 column volumes PBS before elution of Qβ VLP was initiated by a step to HSB. Qβ VLP for further processing eluted between 0.6 and 1.8 column volumes after the step to HSB. Qβ VLP containing peak fractions were pooled and stored at 4° C.

TABLE 3

Composition of process solutions for cHA chromatography

| | Buffers | | |
|---|---|---|---|
| Component | HSB | NaPP pH 7.0 | PBS |
| $Na_2HPO_4 \cdot 2H_2O$ | 176.4 mM | 10.70 mM | 15.15 mM |
| $NaH_2PO_4 \cdot 2H_2O$ | 23.60 mM | 9.30 mM | 4.85 mM |
| NaCl | 900 mM | — | 150 mM |

Example 6

Screening for Suitable Chromatography Media

The chromatography media listed below were tested for their affinity for Qβ VLP.

Fractogel® EMD TMAE (M) particle size 40-90 μm, Merck, Darmstadt, Germany (Order No. 1.16881.0500 for 500 ml)

Fractogel® EMD TMAE Hicap (M) particle size 40-90 μm, Merck, Darmstadt, Germany (Order No. 1.10316.0100 for 100 ml)

Fractoprep® DEAE particle size 30-150 μm, Merck, Darmstadt, Germany (Order No. 1.17971.0010 for 10 ml)

Fractoprep® TMAE particle size 30-150 μm, Merck, Darmstadt, Germany (Order No. 1.17973.0100 for 100 ml)

Macro-Prep® CHT Ceramic Hydroxyapatite Type I, 80 μm particle size, Bio-Rad Laboratories, Hercules, USA (Order No. 157-0080 for 100 g)

Macro-Prep® CHT Ceramic Hydroxyapatite Type II, 80 μm particle size, Bio-Rad Laboratories, Hercules, USA (Order No. 157-8000 for 100 g)

Matrex® Granular Silica PEI-300 Å particle size 35-70 μm, Millipore, Bedford, USA (Catalogue Number: 84912 for 100 g)

Matrex® Granular Silica PEI-1000 Å particle size 35-70 μm, Millipore, Bedford, USA (Catalogue Number: 84959 for 100 g)

Poros 50 HQ, PerSeptive Biosystems, Framingham, USA (Order No. 1-2559-03 for 25 ml)

Q Sepharose XL, GE Healthcare, Piscataway, USA (Order No. 17-5072-01 for 300 ml)

Unosphere Q Bio-Rad Laboratories, Hercules, USA (Order No. 156-0101 for 25 ml)

Testing was performed essentially as follows: Qβ VLP solutions from different process stages containing 0-200 mM NaCl in different buffer systems at pH values between 7.0 and 8.0 were applied on small scale columns packed with the respective column matrix and unbound material was washed out with running buffer. Bound components from the sample were eluted either by linear or step gradients during which the concentrations of either salt or buffer components or both were raised. The observed elution profiles were interpreted in terms of binding capacity and selectivity of elution. Fractogel® EMD TMAE (M), Fractogel® EMD TMAE Hicap (M) and Macro-Prep® CHT Ceramic Hydroxyapatite Type II could be identified as chromatography matrices showing a binding capacity which is most suitable for a large scale production.

Example 7

Determination of Qβ VLP by Analytical Size Exclusion Chromatography

Analysis of Qβ particles by analytical size exclusion chromatography was performed using a TskgelG5000 PWXL-column (10 μm, 7.8×300 mm, TosoH Biosep; Cat.-No. 08023) equilibrated in phosphate buffered saline (20 mM $Na_2HPO_4/NaH_4PO_4$, 150 mM NaCl pH 7.2). Run conditions for the analysis are summarized in Table 4.

TABLE 4

| Run conditions for SE-HPLC analysis of Qβ VLP | |
|---|---|
| Flow | 0.8 ml/min |
| Running buffer | 20 mM Na$_2$HPO$_4$/NaH$_2$PO$_4$ 150 mM NaCl pH 7.2 |
| Sample concentration | 1 mg/ml |
| Injection volume | 40 µl |
| Column temperature | 25° C. |
| Run time per sample | 20 minutes |

Purity of Qβ VLP was determined by integration of the peaks in the elution profile at 260 mm.

Example 8

Selection of a Suitable Membrane for Clarification of Cell Homogenates by TFF

TFF membranes suitable for the processing of high viscosity media with different pore sizes were tested. These membranes included the devices listed below:

Pellicon 2 Mini Filter Module, 0.45 µm-Durapore membrane, screen V, filter area 0.1 m², Bedford, Mass., USA (Cat. No. P2HVMPV01)

Pellicon 2 Mini Ultrafiltration Module, 1000 kD-Biomax membrane, screen C, filter area 0.1 m², Bedford, Mass., USA (Cat. No. P2B01MC01)

Sartocon Slice Microfiltration Cassette, 0.2 µm-Hydrosart membrane, open channel, membrane area 0.1 m², Sartorius, Germany (Cat. No. 305 186 07 01 O-SG)

Centramate Tangential Flow Filtration Cassette, 0.45 µm-Supor membrane, suspended screen, membrane area 0.1 m², Pall, USA (Order No. PS M45 C11)

Ultran-Slice Membrane Cassette, 0.2 µm -PES membrane, open channel, membrane area 0.1 m², Schleicher & Schuell, Germany (Order No. 10478685).

Homogenate prepared according to Example 1 (with and without the final 1:2 dilution step) was diafiltrated over the respective membrane against EB⁻-buffer (50 mM Tris·HCl pH 8.0, 5 mM EDTA). The achievable permeate flow across the membrane was investigated in addition to protein concentration and relative content of Qβ VLP in the recovered permeate. Pore sizes smaller than 0.22 µm led to effective retention of Qβ VLP while pore sizes larger than 0.45 µm were assumed to severely impede sterile filtration of the permeate solution. Best results could be obtained with 0.45 µm pore size.

Example 9

Re-Buffering by Size Exclusion Chromatography

The size exclusion chromatography is performed as follows: Pooled peak fractions from the separation on Macro-Prep ceramic Hydroxyapatite Type II are loaded on a Sepharose CL-4B column (bed volume of 1500-1750 ml for sample derived from 80 g cell wet weight, bed height 45-75 cm) equilibrated in PBS buffer (20 mM Na$_2$HPO$_4$/NaH$_2$PO$_4$, 150 mM NaCl pH 7.2). Elution is achieved by isocratic elution with PBS buffer. Symmetrical fractionation of the Qβ VLP main peak is initiated 0.475 column volumes after start of the loading procedure. The desalted Qβ VLP solution is filtrated via a 0.22 µm pore width sterilizing grade filter unit, aliquoted and stored at −80° C.

Example 10

Analysis of Endotoxin Content in Qβ VLP Solutions

Testing for endotoxin contamination of Qβ VLP containing solutions was performed as laid out in Pharm Eur 2.6.14. Method E using either Biowhittaker Kinetic-QCL® Kinetic Chromogenic Assay or Charles River Endochrome-K™ kits. Results usually obtained with the purification procedure presented here are in the range of 0.5-5 EU/100 µg Qβ VLP.

Example 11

Purification of AP205 VLP

AP205 VLP is purified from bacteria expressing AP205 capsid protein following the procedure of Examples 1, 3, 4, and 9. The endotoxin content of the preparation is between 0.5-5 EU/100 µg AP205 VLP as determined according to Pharm Eur 2.6.14. Method E using either Biowhittaker Kinetic-QCL® Kinetic Chromogenic Assay or Charles River Endochrome-K™ kits.

Example 12

Purification of HBc VLP

HBc VLP is purified from bacteria expressing the protein of SEQ ID NO:1 or SEQ ID NO:2, essentially following the procedure of Examples 1, 3, 4, and 9. The endotoxin content of the preparation is between 0.5-5 EU/100 µg HBc VLP as determined according to Pharm Eur 2.6.14. Method E using either Biowhittaker Kinetic-QCL® Kinetic Chromogenic Assay or Charles River Endochrome-K™ kits.

Example 13

Oxidation of Qβ VLP

The oxidation step was performed as follows: Sterile filtrated cleared cell homogenate produced either by TFF (Example 2) or by centrifugation (Example 3) or a combination thereof was stirred for 12 hours in a container that allowed free circulation of air to the surface of the solution. Stirring was performed in way that allowed maximum dissolution of oxygen in the solution without causing foaming. The mature Qβ VLP solution, containing an appropriate amount of disulfide bonds, is filtrated via a 0.22 µm pore width sterilizing grade filter unit.

Example 14

Chromatography on Hydrophobic Interaction Chromatography Matrices

Chromatography on Phenyl Sepharose™ High Performance was performed as follows: A peak fraction from the separation on Fractogel EMD TMAE was adjusted to 1.0 M (NH$_4$)$_2$SO$_4$ in 20 mM sodium phosphate buffer pH 7.2 and loaded on a Phenyl Sepharose™ High Performance column (10 mg VLP/ml bed volume) equilibrated in NaPP-buffer pH 7.2 containing 1.0 M (NH$_4$)$_2$SO$_4$. Unbound sample was eluted with 5 column volumes equilibration buffer before elution of Qβ VLP was initiated by a linear gradient to NaPP-buffer pH 7.2 over 10 column volumes. Qβ VLP for further processing eluted between 3.0 and 7.0 column volumes after the start of the gradient. Qβ VLP containing peak fractions were pooled and stored at 4° C.

Example 15

Chromatography on Immobilized Metal Ion Affinity Chromatography Matrices

A Chelating Sepharose™ Fast Flow column was loaded with $Zn^{2+}$-ions essentially according to the manufacturer's instructions in the following way:
wash with deionized water: 5 CV
charge with 0.2 M ZnSO4: 5 CV
wash with deionized water: 5 CV
wash with elution buffer 1 (20 mM NaPP, 1 M NaCl, pH 5.0): 5 CV
wash with deionized water: 5 CV
sanitization: 0.5 M NaOH; contact time: 5 h
equilibration: 20 mM NaPP-buffer, 1 M NaCl, pH 7.2 (5 CV)

Chromatography on Chelating Sepharose™ Fast Flow was performed as follows: 10 mg of a peak fraction from the separation on Fractogel EMD TMAE were loaded per ml bed volume of a column prepared according to the procedure above and the flow through was collected. The loaded protein could be recovered quantitatively in the flow through while residual proteins from the expression host were reduced significantly.

The invention claimed is:

1. A process for the purification of a VLP from a recombinant bacterial host expressing said VLP, wherein said VLP comprises recombinant coat protein of an RNA bacteriophage, the process comprising the steps of:
   (a) homogenizing said bacterial host;
   (b) clarifying the homogenate obtained by said homogenizing;
   (c) purifying said VLP from the clarified homogenate obtained by said clarifying in a first chromatography comprising the steps of:
      (i) binding said VLP to a first chromatography matrix, wherein said first chromatography matrix is a tentacle anion exchange matrix;
      (ii) washing said first chromatography matrix; and
      (iii) eluting said VLP from said first chromatography matrix; and
   (d) further purifying said VLP from the eluate obtained by said first chromatography in a second chromatography, wherein said second chromatography is performed on a second chromatography matrix, wherein said second chromatography matrix is a hydroxyapatite matrix;
   wherein said steps are performed in the given order.

2. The process of claim 1, wherein said second chromatography comprises the steps of:
   (i) binding said VLP to said second chromatography matrix, wherein said second chromatography matrix is a hydroxyapatite matrix;
   (ii) washing said second chromatography matrix; and
   (iii) eluting said VLP from said second chromatography matrix;
   wherein said steps are performed in the given order.

3. The process of claim 1, said process additionally comprising the step of finally purifying said VLP obtained by said second chromatography by at least one third chromatography, wherein said at least one third chromatography is selected from:
   (a) hydrophobic interaction chromatography (HIC);
   (b) immobilized metal ions affinity chromatography (IMAC); and
   (c) size exclusion chromatography.

4. The process of claim 1, wherein said clarifying of said homogenate is performed by a method selected from the group consisting of:
   (a) centrifugation;
   (b) tangential flow filtration; and
   (c) a combination of (a) and (b).

5. The process of claim 1, wherein said first chromatography matrix is a tentacle anion exchange matrix comprising (i) resin particles of cross-linked methacrylate polymer or cross-linked vinyl polymer, and (ii) acrylamide tentacles, wherein said acrylamide tentacles are attached to the surface of said resin particles, and wherein said acrylamide tentacles are substituted with TMAE (Trimethylaminoethyl-) groups.

6. The process of claim 1, wherein said first chromatography comprises the steps of:
   (i) equilibrating said first chromatography matrix with a first equilibration buffer;
   (ii) binding said VLP to a first chromatography matrix;
   (iii) washing said first chromatography matrix with a first washing buffer; and (iv) eluting said VLP from said first chromatography matrix with a first elution puffer;
   wherein said first equilibration buffer, said first washing buffer and said first elution buffer comprise potassium chloride or sodium chloride.

7. The process of claim 6, wherein said first equilibration buffer comprises at most about 200 mM sodium chloride, said first washing buffer comprises about 425 mM sodium chloride, and said first elution buffer comprises least about 500 mM sodium chloride or a gradient of sodium chloride, wherein said gradient is from at most about 400 to at least about 650 mM sodium chloride.

8. The process of claim 6, wherein said first equilibration buffer, said first washing buffer and said first elution buffer comprise a pH of about 7.2.

9. The process of claim 1, wherein said hydroxyapatite matrix is a ceramic hydroxyapatite matrix.

10. The process of claim 2, wherein said second chromatography comprises the steps of:
    (i) equilibrating said second chromatography matrix with a second equilibration buffer;
    (ii) binding said VLP to said second chromatography matrix, wherein said second chromatography matrix is a hydroxyapatite matrix;
    (ii) washing said second chromatography matrix with a second washing buffer; and
    (iii) eluting said VLP from said second chromatography matrix;
    wherein said second equilibration buffer, said second washing buffer and said second elution buffer, comprise potassium chloride or sodium chloride.

11. The process of claim 10, wherein said second equilibration buffer comprises about 100 to 400 mM sodium chloride, said second washing buffer comprises about 150 mM sodium chloride, and said second elution buffer comprises 900 mM sodium chloride and about 200 mM sodium phosphate buffer.

12. The process of claim 10, wherein said second equilibration buffer, said second washing buffer and said second elution buffer comprise a pH of about 7.2.

13. The process of claim 1, wherein said clarifying further comprises the step of exposing said VLP to oxidative conditions.

14. The process of claim 3 wherein said least one third chromatography is at least one size exclusion chromatography.

15. A process for the purification of a VLP of RNA bacteriophage Qβ from a recombinant bacterial host expressing said VLP, the process comprising the steps of:
    (a) homogenizing said bacterial host;
    (b) clarifying the homogenate obtained by said homogenizing, wherein said clarifying further comprises the step of exposing said VLP to oxidative conditions;
    (c) purifying said VLP from the clarified homogenate obtained by said clarifying in a first chromatography comprising the steps of:
       (i) equilibrating a tentacle anion exchange matrix, wherein said equilibrating is performed with a first equilibration buffer, wherein said first equilibration buffer comprises about 150 mM sodium chloride and a pH of 7.2;
       (ii) binding said VLP to said tentacle anion exchange matrix ;
       (iii) washing said tentacle anion exchange matrix , wherein said washing is performed with a first washing buffer comprising about 425 mM sodium chloride and a pH of 7.2; and
       (iv) eluting said VLP from said tentacle anion exchange matrix, wherein said eluting is performed with a first elution buffer comprising a gradient of 425 to 650 mM sodium chloride and a pH of 7.2;
    wherein said tentacle anion exchange matrix comprises (i) resin particles of cross-linked methacrylate polymer or cross-linked vinyl polymer, and (ii) acrylamide tentacles, wherein said acrylamide tentacles are attached to the surface of said resin particles, and wherein said acrylamide tentacles are substituted with TMAE (Trimethylaminoethyl-) groups;

(d) further purifying said VLP from the eluate obtained by said first chromatography in a second chromatography comprising the steps of:
  (i) equilibrating a hydroxyapatite matrix wherein said equilibrating is performed with a second equilibration buffer comprising about 150 mM sodium chloride and a pH of 7.2;
  (ii) binding said VLP to hydroxyapatite matrix;
  (iii) washing said hydroxyapatite matrix, wherein said washing is performed with a second washing buffer comprising about 150 mM sodium chloride and a pH of 7.2;
  (iv) eluting said VLP from said hydroxyapatite matrix, wherein said eluting is performed with a second elution buffer comprising about 900 mM sodium chloride, about 200 mM sodium phosphate buffer and a pH of 7.2;
  wherein said hydroxyapatite matrix is a ceramic hydroxyapatite matrix;

(e) finally purifying said VLP contained in the eluate of said second chromatography by exactly one size exclusion chromatography, wherein said size exclusion chromatography is performed in the presence of about 150 mM sodium chloride;

wherein said steps are performed in the given order.

16. A process for the purification of a VLP of RNA bacteriophage AP205 from a recombinant bacterial host expressing said VLP, the process comprising the steps of:
  (a) homogenizing said bacterial host;
  (b) clarifying the homogenate obtained by said homogenizing, wherein said clarifying further comprises the step of exposing said VLP to oxidative conditions;
  (c) purifying said VLP from the clarified homogenate obtained by said clarifying in a first chromatography comprising the steps of:
    (i) equilibrating a tentacle anion exchange matrix, wherein said equilibrating is performed with a first equilibration buffer, wherein said first equilibration buffer comprises about 150 mM sodium chloride and a pH of 7.2;
    (ii) binding said tentacle anion exchange matrix;
    (iii) washing said tentacle anion exchange matrix, wherein said washing is performed with a first washing buffer comprising about 425 mM sodium chloride and a pH of 7.2; and
    (iv) eluting said VLP from said tentacle anion exchange matrix, wherein said eluting is performed with a first elution buffer comprising about 550 mM sodium chloride and a pH of 7.2;

wherein said tentacle anion exchange matrix comprises (i) resin particles of cross-linked methacrylate polymer or cross-linked vinyl polymer, and (ii) acrylamide said acrylamide tentacles, wherein said acrylamide tentacles are attached to the surface of said resin particles, and wherein said acrylamide tentacles are substituted with TMAE (Trimethylaminoethyl-) groups;

(d) further purifying said VLP from the eluate obtained by said first chromatography in a second chromatography comprising the steps of:
    (i) equilibrating a hydroxyapatite matrix, wherein said equilibrating is performed with a second equilibration buffer comprising, about 100 mM sodium chloride and about 5 mM sodium phosphate buffer and a pH of 7.2;
    (ii) binding said VLP to said hydroxyapatite matrix;
    (iii) washing said hydroxyapatite matrix wherein said washing is performed with a second washing buffer comprising about 100 mM sodium chloride, about 5 mM sodium phosphate buffer and a pH of 7.2;
    (iv) eluting said VLP from said hydroxyapatite matrix, wherein said eluting is performed with a second elution buffer comprising about 250 mM sodium chloride, about 50 mM sodium phosphate buffer and a pH of 7.2;
    wherein said hydroxyapatite matrix is a ceramic hydroxyapatite matrix;

(e) finally purifying said VLP contained in the eluate of said second chromatography by exactly one size exclusion chromatography, wherein said size exclusion chromatography is performed in the presence of about 150 mM sodium chloride;

wherein said steps are performed in the given order.

17. The process of claim 1, wherein said RNA bacteriophage is bacteriophage Qβ, and wherein said coat protein consists of the amino acid sequence of SEQ ID NO:3.

18. The process of claim 1, wherein said RNA bacteriophage is bacteriophage AP205, and wherein said coat protein consists of the amino acid sequence of SEQ ID NO:16.

19. The process of claim 1, wherein the tentacles of said tentacle anion exchange matrix are substituted with functional groups selected from the group consisting of:
  (a) trimethylaminoethyl- (TMAE);
  (b) dimethylaminoethyl- (DMAE); and
  (c) diethylaminoethyl- (DEAE).

20. The process of claim 9, wherein said ceramic hydroxyapatite matrix comprises a particle size of about 80 μm and a pore size of the particles of about 800-1000 Å.

* * * * *